US009717715B2

(12) United States Patent
Lee et al.

(10) Patent No.: US 9,717,715 B2
(45) Date of Patent: *Aug. 1, 2017

(54) METHOD OF COMBINATION THERAPY USING AN ANTI-C-MET ANTIBODY

(71) Applicant: Samsung Electronics Co., Ltd., Suwon-si, Gyeonggi-do (KR)

(72) Inventors: Seung Hyun Lee, Suwon-si (KR); Geun Woong Kim, Yongin-si (KR); Kyung Ah Kim, Seongnam-si (KR); Hye Won Park, Pyeongtaek-si (KR); Ho Yeong Song, Seongnam-si (KR); Young Mi Oh, Incheon (KR); Saet Byoul Lee, Seoul (KR); Ji Min Lee, Seoul (KR); Kwang Ho Cheong, Seoul (KR); Yun Ju Jeong, Hwaseong-si (KR); Mi Young Cho, Seoul (KR); Jae Hyun Choi, Seongnam-si (KR); Yun Jeong Song, Seongnam-si (KR); Yoon Aa Choi, Busan (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 234 days.

This patent is subject to a terminal disclaimer.

(21) Appl. No.: 14/081,886

(22) Filed: Nov. 15, 2013

(65) Prior Publication Data

US 2015/0140014 A1 May 21, 2015

(51) Int. Cl.
| | |
|---|---|
| A61K 39/395 | (2006.01) |
| A61K 31/437 | (2006.01) |
| A61K 31/517 | (2006.01) |
| A61K 31/44 | (2006.01) |
| C07K 16/28 | (2006.01) |
| C12N 5/16 | (2006.01) |

(52) U.S. Cl.
CPC ........... *A61K 31/437* (2013.01); *A61K 31/44* (2013.01); *A61K 31/517* (2013.01); *A61K 39/3955* (2013.01); *A61K 39/39558* (2013.01); *C07K 16/2863* (2013.01); *C12N 5/163* (2013.01); *C07K 2317/24* (2013.01); *C07K 2317/53* (2013.01); *C07K 2317/565* (2013.01); *C07K 2317/622* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,300,065 B1 | 10/2001 | Kieke et al. | |
| 6,699,658 B1 | 3/2004 | Wittrup et al. | |
| 8,066,994 B2 | 11/2011 | Gillies et al. | |
| 2005/0054019 A1 | 3/2005 | Michaud et al. | |
| 2009/0226443 A1* | 9/2009 | Filvaroff et al. | 424/138.1 |
| 2010/0115639 A1 | 5/2010 | Goetsch | |
| 2010/0129369 A1 | 5/2010 | Davies et al. | |
| 2010/0226925 A1 | 9/2010 | Dillon et al. | |
| 2010/0254989 A1 | 10/2010 | Bossenmaier et al. | |
| 2011/0064653 A1 | 3/2011 | Hansen et al. | |
| 2011/0097262 A1 | 4/2011 | Goetsch et al. | |
| 2011/0104176 A1 | 5/2011 | Cheong et al. | |
| 2011/0239316 A1 | 9/2011 | Goetsch et al. | |
| 2011/0263830 A1 | 10/2011 | Goetsch et al. | |
| 2013/0089556 A1 | 4/2013 | Cheong et al. | |

FOREIGN PATENT DOCUMENTS

| | | |
|---|---|---|
| EP | 2 316 484 A1 | 5/2011 |
| KR | 10-2011-0091519 A | 8/2011 |
| KR | 10-2011-0097839 A | 8/2011 |
| WO | WO 2010/063746 A1 | 6/2010 |
| WO | WO 2010/064090 A1 | 6/2010 |
| WO | WO 2010/069765 A1 | 6/2010 |
| WO | WO 2011/110642 A2 | 9/2011 |

OTHER PUBLICATIONS

US 6,331,391, 12/2001, Wittrup et al. (withdrawn)
Rudikoff et al, Proc. Natl. Acad. Sci. USA, 79(6):1979-1983, Mar. 1982.*
MacCallum et al, J. Mol. Biol., 262, 732-745, 1996.*
Pascalis et al, Journal of Immunology, 2002, vol. 169, pp. 3076-3084.*
Casset et al, Biochemical and Biophysical Research Communications, 2003, vol. 307, pp. 198-205.*
Holm et al, Molecular Immunology, 2007, vol. 44, pp. 1075-1084.*
Granziero et al, Eur. J. Immunol. 1999, 29:1127-1138.*
Byers, T., CA Journal, vol. 49, No. 6, Nov./Dec. 1999.*
Ben-Efraim, Tumor Biology 1999; 20: 1-24.*
Paul, William E., Fundamental Immunology, $3^{rd}$ Edition, pp. 292-295, (1993).
Panka et al., Proceedings of the National Academy of Sciences, U.S.A., vol. 85, p. 3080-3084, (1988).
Johnson, George and Wu, Tai Te, Methods in Molecular Biology: Antibody Engineering: Methods and Protocols, vol. 248, p. 11-25 (2004).
Portolano, Stefano et al., The Journal of Immunology, vol. 150, No. 3, p. 880-887 (1993).
Bendig, Mary M., Methods: A Companion to Methods in Enzymology, vol. 8, p. 83-93 (1995).
Beiboer et al., "Guided Selection of a Pan Carcinoma Specific Antibody Reveals Similar Binding Characteristics yet Structural Divergence Between the Original Murine Antibody and its Human Equivalent", *J. Mol. Biol.*, 296-: 833-849 (2000).

(Continued)

Primary Examiner — Mark Halvorson
(74) Attorney, Agent, or Firm — Leydig, Voit & Mayer, Ltd,

(57) ABSTRACT

A method for prevention or treatment of a cancer, comprising co-administering (a) an anti-c-Met antibody or an antigen-binding fragment thereof, and (b) at least one of lapatinib, regorafenib, vemurafenib or a combination thereof, to a subject in need thereof, and a pharmaceutical composition comprising (a) an anti-c-Met antibody or an antigen-binding fragment thereof, and (b) at least one of lapatinib, regorafenib, vemurafenib, or a combination thereof are provided.

6 Claims, 26 Drawing Sheets

(56) References Cited

OTHER PUBLICATIONS

Kabat et al., "Attempts to Locate Complimentarity-Determining Residues in the Variable Positions of Light and Heavy Chains*", *Annals New York Academy of Sciences*, 190: 382-393 (1971).
Klimka et al., "Human anti-CD30 recombinant antibodies by guided phage antibody selection using cell panning", *British Journal of Cancer*, 83(2): 252-260 (2000).
Macallum et al., "Antibody-antigen Interactions: Contact Analysis and Binding Site Topography", *J. Mole. Biology*, 262:732-745 (1996).
Munodzana et al., "Conformational Dependence of *Anaplasma marginale* Major Surface Protein 5 Surface-Exposed B-Cell Epitopes", *Infection and Immunity*, 66(6): 2619-2624 (1998).
De Pascalis et al., "Grafting of 'Abbreviated' Complimentarity-Determining Regions Containing Specificity-Determining Residues Essential for Ligand Contact to Engineer a Less Immunogenic Humanized Monoclanal Antibody", *The Journal of Immunology*, 169: 3076-3084 (2002).
Polyak et al., "Alanine-170 and proline-172 are critical determinants for extracellular CD20 epitopes; heterogeneity in the fine specificity of CD20 monoclanal antibodies is defined by additional requirements imposed by both amino acid sequence and quaternary structure", *Blood*, 99(9): 3256-3262 (2002).
Rudikoff et al., "Single amino acid substitution altering antigen-binding specificity", *Proceedings of the National Academy of Sciences USA*, 79: 1979-1983 (1982).
Vajdos et al., "Comprehensive Functional Maps of the Antigen-binding Site of an Anti-ErbB2 Antibody Obtained with Shotgun Scanning Mutagenesis", *J. Mol. Biol.*, 320: 415-428 (2002).
Zemlin et al., "Expressed Murine and Human CDR-H3 Intervals of Equal Length Exhibit Distinct Repertoires that Differ in their Amino Acid Composition and Predicted Range of Structures", *Journal of Molecular Biology*, 334; 733-749 (2003).
Barderas, *PNAS*, 105(26): 9029-9034 (2008).
Fermer, *Tumor Biology*, 25: 7-13 (2004).
Yau, *J. Immunol. Methods*, 297: 213-224 (2005).
Korean Intellectual Property Office, International Search Report in corresponding International Patent Application No. PCT/KR2012/008089, mailed Mar. 18, 2013.

* cited by examiner

METHOD OF COMBINATION THERAPY USING AN ANTI-C-MET ANTIBODY

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 89,250 Byte ASCII (Text) file named "714388sequencelisting_revised_20151013.txt" created on Oct. 13, 2015.

BACKGROUND

1. Field

The present disclosure relates to a method for prevention or treatment of a cancer, comprising co-administering (a) an anti-c-Met antibody or an antigen-binding fragment thereof, and (b) at least one of lapatinib, regorafenib, vemurafenib or a combination thereof, to a subject in need thereof and a pharmaceutical composition comprising (a) an anti-c-Met antibody or an antigen-binding fragment thereof, and (b) at least one of lapatinib, regorafenib, vemurafenib, or a combination thereof.

2. Description of the Related Art c-Met is a receptor for hepatocyte growth factor (HGF), a cytokine that binds the extracellular region of the c-Met receptor tyrosine kinase to induce cell division, movement, morphogenesis, and angiogenesis of various normal cells and tumor cells. c-Met is a representative receptor tyrosine kinase existing on the surface of cells, is itself a proto-oncogene, and is sometimes involved in various mechanisms related to cancer, such as cancer development, metastasis, migration, invasion, and angiogenesis, independent from a ligand, HGF. Thus, c-Met has been recently emerging as a new target for anti-cancer therapy.

In particular, c-Met is known to be involved in induction of resistance to commonly used anti-cancer drugs, and thus is regarded as important with respect to personalized treatments. Representative anti-cancer therapeutic drugs targeting epidermal growth factor receptor EGFR (ERBB1), i.e., Eribitux or Tarceva, work by blocking the signaling related to cancer development. In addition, Herceptin, which is well known as a breast cancer therapeutic drug, targets ERBB2 (HER2) and works by blocking the transduction of signals necessary for cell proliferation. Among patients resistant to the drugs described above, the signal transduction pathway that induces cell proliferation is not blocked due to the overexpression of c-Met. Thus, c-met has emerged as a target of interest for many pharmaceutical companies. Still, there is a need for additional anti-c-Met antibodies and related methods and compositions.

SUMMARY

Provided is an anti-c-Met antibody or an antigen-binding fragment thereof. In one aspect, the anti-c-Met antibody or antigen-binding fragment thereof comprises a heavy chain variable region comprising at least one heavy chain complementarity determining region (CDR) selected from the group consisting of CDR-H1 having an amino acid sequence of SEQ ID NO: 4, CDR-H2 having an amino acid sequence of SEQ ID NO: 5, and CDR-H3 having an amino acid sequence of SEQ ID NO: 6; and a light chain variable region comprising at least one light chain CDR selected from the group consisting of CDR-L1 having an amino acid sequence of SEQ ID NO: 7, CDR-L2 having an amino acid sequence of SEQ ID NO: 8, and CDR-L3 having an amino acid sequence of SEQ ID NO: 9, wherein SEQ ID NOs: 4 to 9 are respectively represented by Formulas I to VI, described herein. In another aspect, the anti-c-Met antibody or antigen-binding fragment thereof comprises a heavy chain variable region comprising at least one heavy chain complementarity determining region (CDR) selected from the group consisting of CDR-H1 having an amino acid sequence of SEQ ID NO: 1, CDR-H2 having an amino acid sequence of SEQ ID NO: 2, and CDR-H3 having an amino acid sequence of SEQ ID NO: 3; and a light chain variable region comprising at least one light chain CDR selected from the group consisting of CDR-L1 having an amino acid sequence of SEQ ID NO: 7, CDR-L2 having an amino acid sequence of SEQ ID NO: 8, and CDR-L3 having an amino acid sequence of SEQ ID NO: 9, wherein SEQ ID NOS: 7 to 9 are respectively represented by Formulas IV to VI described herein. Nucleic acids encoding the antibodies and antibody fragments also are provided.

Further provided is a pharmaceutical composition including an anti-c-Met antibody or an antigen-binding fragment thereof, a method for preventing or treating cancer by administering the antibody or antigen-binding fragment thereof, as well as related methods and compositions.

Further provided is a pharmaceutical composition comprising (a) an anti-c-Met antibody or an antigen-binding fragment thereof, and (b) at least one of lapatinib, regorafenib, vemurafenib, or combination thereof; as well as a method for preventing and/or treating cancer by co-administering (a) an anti-c-Met antibody or an antigen-binding fragment thereof, and (b) at least one of lapatinib, regorafenib, vemurafenib, or a combination thereof.

BRIEF DESCRIPTION OF THE DRAWINGS

These and/or other aspects will become apparent and more readily appreciated from the following description of the embodiments, taken in conjunction with the accompanying drawings of which:

FIG. 8A shows the degree of Akt phosphorylation by huAbF46-H4-A1 (U6-HC7), huAbF46-H4-A1 (IgG2 hinge), and huAbF46-H4-A1 (IgG2 Fc) antibodies, and FIG. 8B shows the degree of Akt phosphorylation by huAbF46-H4-A1 (IgG2 Fc) and L3-11Y antibodies;

FIG. 9A shows the degree of degradation of c-Met by huAbF46-H4-A1 (U6-HC7), huAbF46-H4-A1 (IgG2 hinge), and huAbF46-H4-A1 (IgG2 Fc) antibodies, and FIG. 9B shows the degree of degradation of c-Met by huAbF46-H4-A1 (IgG2 Fc) and L3-11Y antibodies.

FIG. 14 shows the results for a NSCLC PDT, and FIG. 15 shows the results for an RCC PDT.

DETAILED DESCRIPTION

Figure 1:
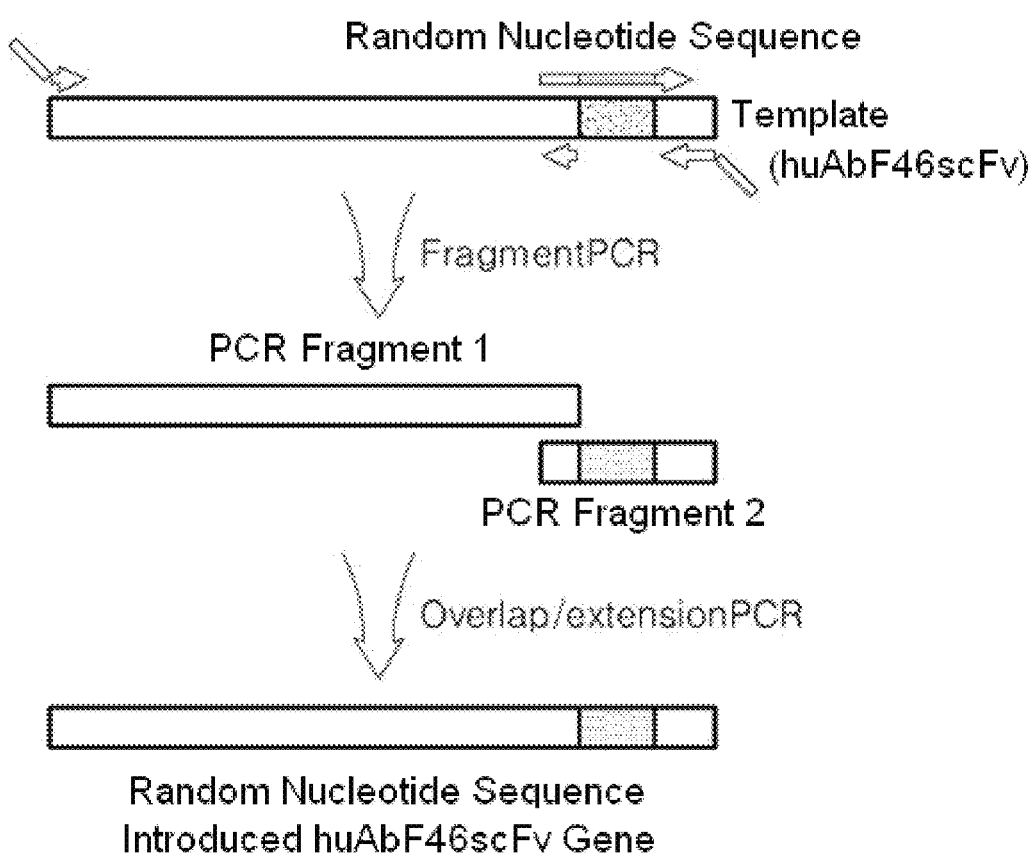
FIG. 1 is a diagram showing the use of overlap extension PCR to obtain a scFv gene library of huAbF46 antibodies in which a desired CDR is mutated.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one" when preceding a list of elements, modify the entire list of elements and do not modify the individual elements of the list.

According to an embodiment, there is provided an anti-c-Met antibody or an antigen-binding fragment thereof, wherein the antibody includes: a heavy chain variable region having the amino acid sequence of at least one heavy chain complementarity determining region (CDR) selected from the group consisting of CDR-H1 having an amino acid sequence of SEQ ID NO: 4, CDR-H2 having an amino acid sequence of SEQ ID NO: 5, and CDR-H3 having an amino acid sequence of SEQ ID NO: 6; and a light chain variable region having the amino acid sequence of at least one light chain complementarity determining region selected from the group consisting of CDR-L1 having an amino acid sequence of SEQ ID NO: 7, CDR-L2 having an amino acid sequence of SEQ ID NO: 8, and CDR-L3 having an amino acid sequence of SEQ ID NO: 9, in which SEQ ID NOS: 4 to 9 are respectively represented by Formula I to VI below:

```
Formula I
                                          (SEQ ID NO: 4)
Xaa1-Xaa2-Tyr-Tyr-Met-Ser Formula II
                                          (SEQ ID NO: 5)
Arg-Asn-Xaa3-Xaa4-Asn-Gly-Xaa5-Thr Formula III
                                          (SEQ ID NO: 6)
Asp-Asn-Trp-Leu-Xaa6-Tyr Formula IV
                                          (SEQ ID NO: 7)
Lys-Ser-Ser-Xaa7-Ser-Leu-Leu-Ala-Xaa8-
Gly-Asn-Xaa9-Xaa10-Asn-Tyr-Leu-Ala Formula V
                                          (SEQ ID NO: 8)
Trp-Xaa11-Ser-Xaa12-Arg-Val-Xaa13

Formula VI
                                          (SEQ ID NO: 9)
Xaa14-Gln-Ser-Tyr-Ser-Xaa15-Pro-Xaa16-Thr
```

In Formula I, $Xaa_1$ is Pro or Ser or absent, and $Xaa_2$ is Glu or Asp.

In Formula II, $Xaa_3$ is Asn or Lys, $Xaa_4$ is Ala or Val, and $Xaa_5$ is Asn or Thr.

In Formula III, $Xaa_6$ is Ser or Thr.

In Formula IV, $Xaa_7$ is His, Arg, Gln, or Lys, $Xaa_8$ is Ser or Trp, $Xaa_9$ is His or Gln, and $Xaa_{10}$ is Lys or Asn.

In Formula V, $Xaa_{11}$ is Ala or Gly, $Xaa_{12}$ is Thr or Lys, and $Xaa_{13}$ is Ser or Pro.

In Formula VI, $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

For example, the CDR-H1 may be a polypeptide having one amino acid sequence selected from the group consisting of amino acid sequences of SEQ ID NOS: 22 to 24, the CDR-H2 may be a polypeptide having an amino acid sequence of SEQ ID NO: 25 or 26, and the CDR-H3 may be a polypeptide having an amino acid sequence of SEQ ID NO: 27 or 28.

Also, the CDR-L1 may be a polypeptide having one amino acid sequence selected from the group consisting of amino acid sequences of SEQ ID NOS: 29 to 33 and 71, CDR-L2 may be a polypeptide having one amino acid sequence selected from the group consisting of amino acid sequences of SEQ ID NOS: 34 to 36, and CDR-L3 may be a polypeptide having one amino acid sequence selected from the group consisting of amino acid sequences of SEQ ID NOS: 13 to 16 or a polypeptide having an amino acid sequence of SEQ ID NO: 37.

According to another embodiment, there is provided an anti-c-Met antibody or antigen binding fragment thereof including: a heavy chain variable region having an amino acid sequence of at least one heavy chain complementarity determining region selected from the group consisting of CDR-H1 having an amino acid sequence of SEQ ID NO: 1, CDR-H2 having an amino acid sequence of SEQ ID NO: 2, and CDR-H3 having an amino acid sequence of SEQ ID NO: 3; and a light chain variable region having an amino acid sequence of at least one light chain complementarity determining region selected from the group consisting of CDR-L1 having an amino acid sequence of SEQ ID NO: 7, CDR-L2 having an amino acid sequence of SEQ ID NO: 8, and CDR-L3 having an amino acid sequence of SEQ ID NO: 9, wherein SEQ ID NOS: 7 to 9 are respectively represented by Formula IV to VI below:

```
Formula IV
                                        (SEQ ID NO: 7)
Lys-Ser-Ser-Xaa7-Ser-Leu-Leu-Ala-Xaa8-Gly-Asn-
Xaa9-Xaa10-Asn-Tyr-Leu-Ala Formula V
                                        (SEQ ID NO: 8)
Trp-Xaa11-Ser-Xaa12-Arg-Val-Xaa13

Formula VI
                                        (SEQ ID NO: 9)
Xaa14-Gln-Ser-Tyr-Ser-Xaa15-Pro-Xaa16-Thr
```

In Formula IV, $Xaa_7$ is His, Arg, Gln, or Lys, $Xaa_8$ is Ser or Trp, $Xaa_9$ is His or Gln, and $Xaa_{10}$ is Lys or Asn.

In Formula V, $Xaa_{11}$ is Ala or Gly, $Xaa_{12}$ is Thr or Lys, and $Xaa_{13}$ is Ser or Pro.

In Formula VI, $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

For example, the light chain variable region may have an amino acid sequence of at least one light chain complementarity determining region selected from the group consisting of CDR-L1 having an amino acid sequence of SEQ ID NO: 10 or 71, CDR-L2 having an amino acid sequence of SEQ ID NO: 11, and CDR-L3 having one amino acid sequence selected from the group consisting of amino acid sequences of SEQ ID NOS: 13 to 16.

By way of further illustration, the heavy chain variable region may have an amino acid sequence of SEQ ID NO: 17, and the light chain variable region may have one amino acid sequence selected from the group consisting of amino acid sequences of SEQ ID NOS: 18 to 21 and 72.

The terms "c-Met" or "c-Met protein" may refer to a receptor tyrosine kinase (RTK) that binds to a hepatocyte growth factor (HGF). c-Met can be a c-Met protein from any species, particularly a mammal or primate, for instance, human c-Met (e.g., NP_000236), or monkey c-Met (e.g., Macaca mulatta, NP_001162100), or rodents such as mouse c-Met (e.g., NP_032617.2), rat c-Met (e.g., NP_113705.1), and the like. The c-Met protein may include a polypeptide encoded by the nucleotide sequence identified as GenBank Accession Number NM_000245, a polypeptide having the amino acid sequence identified as GenBank Accession Number NP_000236 or extracellular domains thereof. The receptor tyrosine kinase c-Met participates in various mechanisms, such as cancer development, metastasis, migration of cancer cell, invasion of cancer cell, and angiogenesis.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies are developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDR of animal-derived antibodies. Antibody database, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti-c-Met antibodies may be mouse-derived antibodies, mouse-human chimeric antibodies, or humanized antibodies. The antibodies or antigen-binding fragments thereof may be one isolated from a living body.

The antibody may be a monoclonal antibody.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma ($\gamma$), mu ($\mu$), alpha ($\alpha$), delta ($\delta$), or epsilon ($\epsilon$) type, which may be further categorized as gamma 1 ($\gamma$1), gamma 2 ($\gamma$2), gamma 3 ($\gamma$3), gamma 4 ($\gamma$4), alpha 1 ($\alpha$1), or alpha 2 ($\alpha$2). The light chain constant region is of either a kappa ($\kappa$) or lambda ($\lambda$) type.

The term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" or "specifically recognized" is well known to one of ordinary skill in the art, and indicates that an antibody and an antigen specifically interact with each other to lead to an immunological activity. The anti-c-Met antibody or an antigen-binding fragment thereof may specifically bind to an epitope comprising 5 or more contiguous amino acids within the SEMA domain of c-Met protein According to an embodiment, the antibody may be an antigen-binding fragment selected from the group consisting of scFv, (scFv)$_2$, Fab, Fab', and F(ab')$_2$.

The term "antigen-binding fragment" used herein refers to fragments of an intact immunoglobulin including portions of a polypeptide including antigen-binding regions having the ability to specifically bind to the antigen. For example, the antigen-binding fragment may be scFv, (scFv)$_2$, Fab, Fab', or F(ab')$_2$, but is not limited thereto. Among the antigen-binding fragments, Fab that includes light chain and heavy chain variable regions, a light chain constant region, and a first heavy chain constant region $C_{H1}$, has one antigen-binding site. The Fab' fragment is different from the Fab fragment, in that Fab' includes a hinge region with at least one cysteine residue at the C-terminal of $C_{H1}$. The F(ab')$_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art. Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

By way of further example, the anti-c-Met antibody or antibody fragment may include a heavy chain with the amino acid sequence of SEQ ID NO: 62 (wherein the amino acid sequence from $1^{st}$ to $17^{th}$ position is a signal peptide) or the amino acid sequence from $18^{th}$ to $462^{nd}$ of SEQ ID NO: 62 and a light chain with the amino acid sequence of SEQ ID NO: 68 (wherein the amino acid sequence from $1^{st}$ to $20^{th}$ position is a signal peptide) or the amino acid sequence from $21^{st}$ to $240^{th}$ position of SEQ ID NO: 68; or a heavy chain with the amino acid sequence of SEQ ID NO: 64 (wherein the amino acid sequence from $1^{st}$ to $17^{th}$ position is a signal peptide) or the amino acid sequence from $18^{th}$ to $461^{st}$ position of SEQ ID NO: 64 and a light chain with the amino acid sequence of SEQ ID NO: 68 or the amino acid sequence from $21^{st}$ to $240^{th}$ position of SEQ ID NO: 68; or a heavy chain with the amino acid sequence of SEQ ID NO: 66 (wherein the amino acid sequence from $1^{st}$ to $17^{th}$ position is a signal peptide) or the amino acid sequence from $18^{th}$ to $460^{th}$ position of SEQ ID NO: 66 and a light chain with the amino acid sequence of SEQ ID NO: 68 or the amino acid sequence from $21^{st}$ to $240^{th}$ position of SEQ ID NO: 68.

Additional examples of anti-c-Met antibodies include those in which the anti-c-Met antibody includes a heavy chain with the amino acid sequence of SEQ ID NO: 62 or the amino acid sequence from $18^{th}$ to $462^{nd}$ position of SEQ ID NO: 62 and a light chain with the amino acid sequence of SEQ ID NO: 70 (wherein the amino acid sequence from $1^{st}$ to $20^{th}$ position is a signal peptide) or the amino acid sequence from $21^{st}$ to $240^{th}$ position of SEQ ID NO: 70; a heavy chain with the amino acid sequence of SEQ ID NO: 64 or the amino acid sequence from $18^{th}$ to $461^{st}$ position of SEQ ID NO: 64 and a light chain with the amino acid sequence of SEQ ID NO: 70 or the amino acid sequence from $21^{st}$ to $240^{th}$ position of SEQ ID NO: 70; or a heavy chain with the amino acid sequence of SEQ ID NO: 66 or the amino acid sequence from $18^{th}$ to $460^{th}$ position of SEQ ID NO: 66 and a light chain with the amino acid sequence of SEQ ID NO: 70 or the amino acid sequence from $21^{st}$ to $240^{th}$ position of SEQ ID NO: 70.

In still other examples, the anti-c-Met antibody may include a heavy chain with the amino acid sequence of SEQ ID NO: 62 or the amino acid sequence from $18^{th}$ to $462^{nd}$ position of SEQ ID NO: 62 and a light chain with the amino acid sequence of SEQ ID NO: 73; a heavy chain with the amino acid sequence of SEQ ID NO: 64 or the amino acid sequence from $18^{th}$ to $461^{st}$ position of SEQ ID NO: 64 and a light chain with the amino acid sequence of SEQ ID NO: 73; or a heavy chain with the amino acid sequence of SEQ ID NO: 66 or the amino acid sequence from $18^{th}$ to $460^{th}$ position of SEQ ID NO: 66 and a light chain with the amino acid sequence of SEQ ID NO: 73.

In an embodiment, the anti-c-Met antibody may include a heavy chain with the amino acid sequence from $18^{th}$ to $460^{th}$ position of SEQ ID NO: 66 and a light chain with the amino acid sequence from $21^{st}$ to $240^{th}$ position of SEQ ID NO: 68; or a heavy chain with the amino acid sequence from $18^{th}$ to $460^{th}$ position of SEQ ID NO: 66 and a light chain with the amino acid sequence of SEQ ID NO: 73.

Also provided herein is a polypeptide comprising the amino acid sequence of SEQ ID NO: 68 or 73. The polypeptide with the amino acid sequence of SEQ ID NO: 70 is a light chain including human kappa (K) constant region, and the polypeptide with the amino acid sequence of SEQ ID NO: 68 is a polypeptide obtained by replacing histidine at position 62 (position 36 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 73 is a polypeptide obtained by replacing serine at position 32 (position 27e according to kabat numbering; positioned within CDR-L1) of the polypeptide with the amino acid sequence from $21^{st}$ to $240^{th}$ positions of SEQ ID NO: 68 with tryptophan. By such replacement, antibodies and antibody fragments comprising such sequences exhibits increased activities, such as c-Met biding affinity, c-Met degradation activity, Akt phosphorylation activity, and the like.

Another embodiment provides a polypeptide having the amino acid sequence of SEQ ID NO: 71, which is useful as a light chain complementarity determining region (CDR-L1). Another embodiment provides a anti-c-Met antibody or an antigen-binding fragment thereof including a light chain complementarity determining region having the amino acid sequence of SEQ ID NO: 71, a light chain variable region having the amino acid sequence of SEQ ID NO: 72, or a light chain having the amino acid sequence of SEQ ID NO: 73, optionally in combination with a heavy chain variable region or heavy chain as described herein, or other heavy chain that provides an anti-c-Met antibody or antibody fragment. The antibody or the antigen-binding fragment thereof exhibits increased c-Met degradation activity and Akt phosphorylation activity, as shown in FIGS. 8B and 9B.

According to another embodiment, there is provided a pharmaceutical composition including the anti-c-Met antibody or the antigen-binding fragment as an active ingredient. The pharmaceutical composition can be used for preventing or treating a cancer or for preventing or inhibition of metastasis of a cancer, and may include a pharmaceutically effective amount of the anti-c-Met antibody or the antigen-binding fragment; and a pharmaceutically acceptable carrier, a diluent, or an excipient.

According to another embodiment, there is provided a pharmaceutical composition including (a) an anti-c-Met antibody or an antigen-binding fragment thereof, and (b) at least one of lapatinib, regorafenib, vemurafenib, or a combination thereof, as active ingredients.

In one particular embodiment, the pharmaceutical composition may be formulated by mixing a pharmaceutically effective amount of an anti-c-Met antibody or an antigen-binding fragment thereof, and a pharmaceutically effective amount of at least one of lapatinib, regorafenib, vemurafenib, or a combination thereof, to be simultaneously administered as a combined mixture.

In another embodiment, a kit for prevention and/or treatment of c-Met and angiogenesis-induced diseases is provided, wherein the kit comprises (a) a first pharmaceutical composition containing a pharmaceutically effective amount of an anti-c-Met antibody or an antigen-binding fragment thereof as an active ingredient, (b) a second pharmaceutical composition containing a pharmaceutically effective amount of at least one of lapatinib, regorafenib, vemurafenib, or a combination thereof as an active ingredient, and (c) a package container housing or otherwise containing or packaging the two compositions together. For instance, the pharmaceutical compositions (a) and (b) can be provided in their own separate containers, and a package container (c) may be provided in the form of a box, plastic wrapping, etc., that packages the two containers together. Alternatively, the package container can be a two-compartment container housing the two compositions (a) and (b).

Any anti-c-Met antibody may be used, particularly any anti-c-Met antibody described herein. Any of the foregoing embodiments of a composition or kit may further comprise additional active ingredients, or the active ingredients may consist essentially of, or consist of, the anti-c-Met antibody and at least one of lapatinib, regorafenib, vemurafenib, or a combination thereof.

In accordance with another embodiment, there is provided a method of combination therapy for prevention and/or treatment of a cancer or for preventing and/or inhibition of metastasis of a cancer, comprising co-administering to a subject (a) a pharmaceutically effective amount of anti-c-Met antibody or an antigen-binding fragment thereof and (b) a pharmaceutically effective amount of at least one of lapatinib, regorafenib, vemurafenib, or combination thereof to a subject in need of prevention and/or treatment of the cancer. The method may further comprise a step of identifying a subject who is in need of the prevention and/or treatment of the cancer, prior to the co-administration step.

In the method of combined therapy, the step of co-administering may be conducted by simultaneously or sequentially, in any order, administering a pharmaceutically effective amount of an anti-c-Met antibody or an antigen-binding fragment thereof and a pharmaceutically effective amount of at least one of lapatinib, regorafenib, vemurafenib, or combination thereof. In the case of sequential administration, the order of administration of each effective ingredient is not limited.

In one embodiment, the method of combination therapy may be performed by administering a composition comprising both a pharmaceutically effective amount of an anti-c-Met antibody or an antigen-binding fragment thereof and a pharmaceutically effective amount of at least one of lapatinib, regorafenib, vemurafenib or combination thereof. In another embodiment, the method of combination therapy may comprise simultaneously administering a pharmaceutically effective amount of an anti-c-Met antibody or an antigen-binding fragment thereof and a pharmaceutically effective amount of at least one of lapatinib, regorafenib, vemurafenib or combination thereof as separate compositions. Alternatively, the method may comprise sequentially performing a first step of administration of a pharmaceutically effective amount an anti-c-Met antibody or an antigen-binding fragment thereof as an active ingredient, and a second step of administration of a pharmaceutically effective amount of at least one of lapatinib, regorafenib, vemurafenib, or a combination thereof as an active ingredient. In the sequential administration, the administration order may be reversed and/or repeated any number of times.

By co-administration of an anti-c-Met antibody or an antigen-binding fragment thereof and at least one of lapatinib, regorafenib, vemurafenib, or a combination thereof, it is believed that a synergistic anti-cancer effect can be obtained. In some embodiments, the synergistic anti-cancer effect obtained by co-administration can allow treatment of a cancer to which the anti-c-Met antibody (as a single active ingredient) exhibits little or no effect (e.g., an anti-c-Met antibody resistant cancer). Unless otherwise stated herein, the treatment of a cancer may include the inhibition of metastasis of a cancer as well.

The cancer may be any cancer associated with c-Met activity or overexpression (high level) of c-Met. The cancer may be any selected from the group consisting of squamous cell carcinoma, small-cell lung cancer, non-small-cell lung cancer, adenocarcinoma of the lung, squamous cell carcinoma of the lung, peritoneal carcinoma, skin cancer, skin or intraocular melanoma, colorectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer (gastric cancer), pancreatic cancer, glioblastoma, cervical cancer, ovarian cancer, liver cancer, bladder cancer, hepatocellular adenoma, breast cancer, colon cancer, large intestine cancer, endometrial or uterine carcinoma, salivary gland tumor, kidney cancer, prostate cancer, vulvar cancer, thyroid cancer, and head and neck cancers. The cancer may include a metastatic cancer as well as a primary cancer.

The pharmaceutical composition may include a pharmaceutically acceptable carrier, a diluent, and/or excipient. The pharmaceutically acceptable carriers included in the composition may include commonly used lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include a lubricant, a wetting agent, a sweetener, a flavor enhancer, an emulsifying agent, a suspension agent, and a preservative.

The pharmaceutical composition may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestions of protein or peptide, an active ingredient must be coated or formulated in a pharmaceutical composition, digestion of which is prevented. In addition, the pharmaceutical composition may be administered by using any device capable of moving an active material toward a target cell.

A suitable dosage of the pharmaceutical composition may depend on many factors, such as formulation methods, administration methods, ages, body weight, gender, and pathologic conditions of patients, diets, administration time, administration route, excretion speed, and reaction sensitivity. The desirable dose of the pharmaceutical composition may be in the range of about 0.001 to 100 mg/kg for an adult. The term "pharmaceutically effective amount" or "therapeutically effective amount" used herein refers to an amount used in preventing or treating cancer and/or angiogenesis-related diseases.

The pharmaceutical composition may be formulated, with a pharmaceutically acceptable carrier and/or an additive, into a unit or a multiple dosage form by a well-known method in the art. In this regard, the formulation may be a solution in oil or an aqueous medium, a suspension, a syrup, an emulsifying solution, an extract, powder, granules, a tablet, or a capsule, and may further include a dispersing or a stabilizing agent. In addition, the pharmaceutical composition may be administered as an individual drug, or together with other drugs, and may be administered sequentially or simultaneously with pre-existing drugs. The pharmaceutical composition includes the antibody or the antigen-binding fragments thereof, and thus may be formulated as an immunoliposome. The liposome containing the antibody may be prepared using a well-known method in the art. The immunoliposome is a lipid composition including phosphatidylcholine, cholesterol, and polyethyleneglycol-derived phosphatidylethanolamine, and may be prepared by a reverse phase evaporation method. For example, Fab' fragments may be adhered to the liposome through a disulfide exchange reaction. A chemical drug, such as doxorubicin, may also be included in the liposome.

According to an embodiment, the antibody or antibody fragment may act as an antagonist against the c-Met protein.

The term "antagonist" is understood to include all molecules that partially or entirely block, inhibit, and/or neutralize at least one biological activity of their targets (e.g., c-Met). For example, the term "antagonist antibody" refers to an antibody that inhibits or decreases the biological activity of an antigen to which the antibody binds (e.g., c-Met). An antagonist may decrease receptor phosphorylation due to binding receptors to ligands, promote degradation, or may incapacitate or destroy cells that are activated by the ligands. Also, an antagonist may completely block interaction between a receptor and a ligand, or may practically decrease the interaction due to tertiary structure change or down regulation of the receptor.

According to another embodiment, there is provided a method of preventing and/or treating a cancer, the method including administering the anti-c-Met antibody or the antigen-binding fragment to a subject in need of preventing and/or treating a cancer. In another embodiment, there is provided a method of preventing and/or inhibiting metastasis of a cancer, the method including administering the anti-c-Met antibody or the antigen-binding fragment to a subject in need of preventing and/or inhibiting metastasis of a cancer. The antibody or antibody fragment may be administered in a pharmaceutically effective amount, and may be administered as a pharmaceutical composition formulated with a pharmaceutically acceptable carrier, a diluent, or excipient, as described herein. The method may further include identifying a subject in need of preventing and/or treating a cancer or preventing and/or inhibiting metastasis of a cancer, prior to the administering step. The cancer is described as above.

According to another embodiment, there is provided the anti-c-Met antibody or the antigen-binding fragment for use in preventing and/or treating a cancer, or preparing a medicament for preventing and/or treating a cancer.

The subject to which the active ingredient(s) or the pharmaceutical composition may be administered includes an animal, such as a mammal. For example, the animal may be a human, dog, cat, or mouse.

According to another embodiment of the present invention, there is provided a nucleic acid encoding an antibody or antigen binding fragment thereof as described herein, as well as a nucleic acid encoding any of the foregoing polypeptides or amino acid sequences. The nucleic acid encoding the antibody or antigen binding fragment thereof may be, for example, DNA or RNA and may optionally be incorporated in a vector, such as an expression vector.

According to another embodiment of the present invention, there is provided a cell comprising a nucleic acid encoding an antibody or antigen binding fragment thereof as described herein, as well as a nucleic acid encoding any of the foregoing polypeptides or amino acid sequences.

According to another embodiment of the present invention, there is provided a method of preparing an antibody or antigen binding fragment thereof as described herein, the method comprising expressing a nucleic acid encoding the antibody or antigen binding fragment thereof in a cell.

One or more embodiments of the present invention will now be described in further detail with reference to the following Examples. However, these examples are for the illustrative purposes only and are not intended to limit the scope of the invention.

Example 1: Preparation of Mouse Antibody AbF46 Against c-Met (1) Immunization of Mice To obtain immunized mice necessary for developing hybridoma cell lines, 100 ug of human c-Met/Fc fusion protein (R&D Systems) and a complete Freund's adjuvant in the same amount were mixed, and the mixture was administered via an intraperitoneal injection to each of five 4 to 6-week-old BALB/c mice (Japan SLC, Inc.). After two weeks, the antigen (half the previously injected amount) was mixed with an incomplete Freund's adjuvant using the same method as described above, and the mixture was administered to each mouse via an intraperitoneal injection. After one week, final boosting was performed, and blood was collected from the tail of each mouse after three days to obtain serum. Then, serum was diluted at 1/1000 with PBS, and an enzyme-linked immunosorbent assay (ELISA) was performed to analyze whether the titer of the antibody recognizing c-Met increased. Afterwards, mice in which a sufficient amount of the antibody was obtained were selected, and a cell fusion process was performed on the selected mice.

(2) Cell Fusion and Preparation of Hybridoma Cells

Three days before a cell fusion experiment, a mixture of 50 ug of PBS and human c-Met/Fc fusion protein was administered via an intraperitoneal injection to each mouse (BALB/c mice; Japan SLC, Inc.). Each immunized mouse was anesthetized, and its spleen located on the left side of the body was then extracted and ground with a mesh to isolate cells, which were mixed with a culture medium (DMEM, GIBCO, Invitrogen) to prepare a spleen cell suspension. The suspension was centrifuged to collect a cell layer. The obtained $1\times10^8$ spleen cells were mixed with $1\times10^8$ myeloma cells (Sp2/0), and the mixture was centrifuged to precipitate the cells. The precipitate was slowly dispersed, treated with 1 ml of 45% (w/v) polyethylene glycol (PEG)

in DMEM, and maintained at 37° C. for one minute before adding 1 ml of DMEM. After introducing additional 10 ml of DMEM, the resultant was maintained in a water bath at 37° C. for 5 minutes. The total amount thereof was made to reach 50 ml, and the resultant was centrifuged. The resulting cell precipitate was re-suspended in an isolation medium (HAT medium) at a concentration of $1\times10^5$ cells/ml to $2\times10^5$ cells/ml. Then, the resultant was distributed to a 96-well plate (0.1 ml per well), which was incubated in a carbon dioxide incubator at 37° C. to prepare the hybridoma cells.

(3) Selection of Hybridoma Cells that Produce Monoclonal Antibodies Against c-Met Protein To select the hybridoma cells that specifically bind to c-Met from the hybridoma cells prepared in operation (2) described above, ELISA was performed to screen for the cells that produced antibodies active against human c-Met/Fc fusion protein and human Fc protein.

50 ul (2 ug/ml) of human c-Met/Fc fusion protein was coated on each well of a microtiter plate, and unreacted antigens were removed by washing. To exclude antibodies binding to Fc, but not to c-Met, the human Fc protein was coated on each well of a different microtiter plate using the same method as above. Then, 50 ul of a hybridoma cell suspension was added to each well of the microtiter plates to react for 1 hour. Then, the microwell plates were washed with a phosphate buffer-tween 20 (TBST) solution to remove unreacted culture medium. Goat anti-mouse IgG-horseradish peroxidase (IgG-HRP) was added thereto, and a reaction was allowed to occur at room temperature for 1 hour, and washing was performed with the TBST solution. Subsequently, a substrate solution (OPD) of peroxidase was added to each well, and the reaction degree was evaluated by measuring the absorption at 450 nm using an ELISA reader. Through this method, hybridoma cell lines that produce antibodies highly specific to the human c-Met protein and not to the human Fc protein were repeatedly selected. A limiting dilution was performed on the obtained hybridoma cell lines to obtain a single clone of hybridoma cell lines producing monoclonal antibodies. The selected hybridoma cell line producing the monoclonal antibody was registered in the Korean Cell Line Bank with accession number KCLRF-BP-00220 (deposited Oct. 6, 2009 with the Korean Cell Line Research Foundation, Cancer Research Institute, Seoul National University College of Medicine, 28 Yongon-dong, Chongno-Gu, Seoul, 110-744, Korea).

(4) Production and Purification of the Monoclonal Antibody

The hybridoma cells obtained in operation (3) described above were cultured in a serum free medium to produce monoclonal antibodies and the monoclonal antibodies were purified.

First, the hybridoma cells cultured in 50 ml of culture medium (DMEM) with 10% (w/v) FBS were centrifuged to obtain a cell precipitate, which was washed with 20 ml of PBS more than twice to remove the FBS. Then, 50 ml of DMEM was introduced to re-suspend the cell precipitate, and the resultant was incubated in a carbon dioxide incubator at 37° C. for 3 days. After centrifugation to remove antibody-producing cells, cell culture including antibodies was isolated and stored at 4° C., or used directly. Antibodies were purified from 50 to 300 ml of the culture using a AKTA purification device (GE Health) equipped with an affinity column (protein G agarose column; Pharmacia, USA), and the purified antibodies were stored by replacing the supernatant with PBS using a filter for protein aggregation (Amicon).

Example 2: Preparation of Chimeric Antibody chAbF46 Against c-Met

Generally, when a mouse antibody is injected into a human for medical purposes, immunogenicity may often occur. Thus, to reduce the immunogenicity, a chimeric antibody chAbF46, in which the constant region is substituted with the amino acid sequence of a human IgG1 antibody, was prepared from the mouse antibody AbF46 prepared in Example 1.

Genes were synthesized such that nucleic acid sequence corresponding to a heavy chain was EcoRI-signal sequence-VH-NheI-CH-TGA-XhoI (SEQ ID NO: 38) and nucleic acid sequence corresponding to a light chain was EcoRI-signal sequence-VL-BsiWI-CL-TGA-XhoI (SEQ ID NO: 39). Then, vectors for expression of a chimeric antibody was constructed by cloning a DNA fragment (SEQ ID NO: 38) having the nucleic acid sequence corresponding to the heavy chain in a pOptiVEC™-TOPO TA Cloning Kit included in an OptiCHO™ Antibody Express Kit (Cat No. 12762-019) manufactured by Invitrogen and a DNA fragment (SEQ ID NO: 39) having the nucleic acid sequence corresponding to the light chain in a pcDNA™3.3-TOPO TA Cloning Kit (Cat No. 8300-01) by using restriction enzymes, EcoRI (NEB, R0101S) and XhoI (NEB, R0146S), respectively.

The constructed vectors were amplified using a Qiagen Maxiprep kit (Cat No. 12662), and vectors including the heavy chain and vectors including the light chain were added to 293T cells ($2.5\times10^7$) at a ratio of about 4:1 (about 80 ug:20 ug) with 360 ul of 2 M $CaCl_2$ and were transfected. Next, the mixture was cultured in a DMEM medium with 10% (w/v) FBS at 37° C. in 5% (v/v) $CO_2$ conditions for 5 hours, and then cultured in a DMEM medium without FBS at 37° C. in 5% (v/v) $CO_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was replaced with a PBS buffer, and thus a final chimeric antibody (hereinafter, chAbF46) was purified.

Example 3: Preparation of Humanized Antibody huAbF46 from Chimeric Antibody chAbF46

(1) Heavy Chain Humanization

For the H1-heavy chain and the H3-heavy chain, the human germline gene most homologous to a VH gene of mouse antibody AbF46 was identified using NCBI Ig Blast. VH3-71 was confirmed to have 83% homology at an amino acid level. CDR-H1, CDR-H2, and CDR-H3 of mouse antibody AbF46 were numbered using Kabat numbering and a CDR portion of mouse antibody AbF46 was introduced in a framework of VH3-71. Amino acids of No. 30 (S→T), No. 48 (V→L), No. 73 (D→N), and No. 78 (T→L) were back-mutated to the amino acid sequence of the original mouse AbF46 antibody, wherein the number of the amino acid is numbered according to Kabat numbering, and thus, the number is common to the VH3-71 and mouse AbF46 antibody. Then, in the H1-heavy chain, the amino acids of No. 83 (R→K) and No. 84 (A→T) were additionally mutated, thereby completing construction of H1-heavy chain (SEQ ID NO: 40) and H3-heavy chain (SEQ ID NO: 41).

For the H4-heavy chain, a framework sequence of a human antibody was obtained, and the VH3 subtype (known to have a sequence similar to the mouse framework sequence of the AbF46 antibody and to be stable) was used to introduce CDR-H1, CDR-H2, and CDR-H3 of mouse antibody AbF46 defined using Kabat numbering. Accordingly, the H4-heavy chain (SEQ ID NO: 42) was constructed.

(2) Light Chain Humanization

For the H1-light chain (SEQ ID NO: 43) and the H2-light chain (SEQ ID NO: 44), the human germline gene most homologous to the VL gene of mouse antibody AbF46 was identified using NCBI Ig Blast. VK4-1 was confirmed to have 75% of homology at the amino acid level. CDR-L1, CDR-L2, and CDR-L3 of mouse antibody AbF46 were defined using Kabat numbering and a CDR portion of mouse antibody AbF46 was introduced into a framework of VK4-1. In the H1-light chain, 3 amino acids of No. 36 (Y→H), No. 46 (L→M), and No. 49 (Y→I) were back-mutated. In the H2-light chain, only one amino acid of No. 49 (Y→I) was back-mutated.

For the H3-light chain (SEQ ID NO: 45), the human germline gene most homologous to the VL gene of mouse antibody AbF46 was identified using NCBI Ig Blast. As a result, VK2-40 in addition to VK4-1 (mentioned above) was chosen. Mouse antibodies AbF46 VL and VK2-40 were confirmed to have 61% homology at an amino acid level. CDR-L1, CDR-L2, and CDR-L3 of mouse antibody AbF46 were defined using Kabat numbering and a CDR portion of the mouse antibody AbF46 was introduced into a framework of VK4-1. In the H3-light chain, 3 amino acids of No. 36 (Y→H), No. 46 (L→M), and No. 49 (Y→I) were back-mutated.

For the H4-light chain (SEQ ID NO: 46), a framework sequence of a human antibody was obtained, and the VK1 subtype (conventionally known to be stable) was used to introduce CDR-L1, CDR-L2, and CDR-L3 of mouse antibody AbF46 defined using Kabat numbering. In the H4-light chain, 3 amino acids of No. 36 (Y→H), No. 46 (L→M), and No. 49 (Y→I) were additionally back-mutated.

Then, vectors for expression of the humanized antibody were constructed by cloning DNA fragments (H1-heavy; SEQ ID NO: 47, H3-heavy; SEQ ID NO: 48, and H4-heavy; SEQ ID NO: 49) having the nucleic acid sequence corresponding to the heavy chain in a pOptiVEC™-TOPO TA Cloning Kit included in an OptiCHO™ Antibody Express Kit (Cat No. 12762-019) manufactured by Invitrogen and DNA fragments (H1-light; SEQ ID NO: 50, H2-light; SEQ ID NO: 51, H3-light; SEQ ID NO: 52, and H4-light; SEQ ID NO: 53) having the nucleic acid sequence corresponding to the light chain in a pcDNA™3.3-TOPO TA Cloning Kit (Cat No. 8300-01) by using restriction enzymes, EcoRI (NEB, R0101 S) and XhoI (NEB, R0146S), respectively.

The constructed vectors were amplified using a Qiagen Maxiprep kit (Cat No. 12662), and vectors including the heavy chain and vectors including the light chain were added to 293T cells (2.5×10$^7$) at a ratio of about 4:1 (about 80 ug: 20 ug) with 360 ul of 2 M CaCl$_2$ and were transfected. Next, the mixture was cultured in a DMEM medium added with 10% (w/v) FBS at 37° C. in 5% (v/v) CO$_2$ conditions for 5 hours, and then cultured in a DMEM medium without FBS at 37° C. in 5% (v/v) CO$_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was exchanged with a PBS buffer, and thus a final humanized antibody (hereinafter, huAbF46) was purified. The combination of the H4-heavy chain and the H4-light chain of humanized huAbF46 were used hereinafter.

Example 4: Preparation of scFv Library of huAbF46 Antibody

Genes for preparing scFv of huAbF46 antibody were designed by using the heavy chain variable region and light chain variable region of huAbF46 antibody. Each of the heavy chain variable region and light chain variable region was designed to have a 'VH-linker-VL' form, in which the linker was designed to have an amino acid sequence of 'GLGGLGGGSGGGGSGGSSGVGS' (SEQ ID NO: 54). A polynucleotide (SEQ ID NO: 55) encoding scFv of huAbF46 antibody designed as described above was synthesized (Bioneer, Inc.), and a vector for expressing the polynucleotide was represented as SEQ ID NO: 56.

Then, resultants expressed by the vector were analyzed, and c-Met specific binding was identified.

Example 5: Preparation of Library Gene for Affinity Maturation (1) Selection of Target CDR and Preparation of Primer For affinity maturation of huAbF46 antibody, 6 complementarity determining regions (CDRs) were defined by 'Kabat numbering' from the prepared mouse antibody AbF46. CDRs are shown in Table 1.

TABLE 1

| CDR | amino acid sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

Primers were prepared as follows in order to randomly introduce sequences of CDRs of antibody. According to existing methods of randomly introducing sequences, N codon was used such that bases could be introduced into sites to be mutated at the same rate (25% A, 25% G, 25% C, and 25% T). However, according to the current embodiment, in order to randomly introduce bases into the CDRs of the huAbF46 antibody, 85% of the first and second nucleotides were preserved among three wild-type nucleotides coding amino acids of each CDR, and 5% of each of the other three bases was introduced. In addition, the primer was designed such that the three bases could be introduced into the third nucleotide (33% G, 33% C, and 33% T).

(2) Preparation of huAbF46 Antibody Library and Identification of Binding Affinity to c-Met The construction of an antibody gene library by randomly introducing sequences into CDRs was performed using the primer prepared in operation (1) described above. A polynucleotide including nucleic acid sequence encoding scFv of the huAbF46 antibody was used as a template. Two PCR fragments were prepared as shown in FIGS. 1 and 6 libraries, respectively targeting the 6 CDRs were constructed by using an overlap extension PCR.

The binding affinities of the wild-type antibody (huAb46) and each antibody derived from the libraries to c-Met were identified. While the binding affinities of most antibodies derived from the libraries to c-Met were lower than that of the wild-type antibody, mutants in which the binding affinity to c-Met was not reduced were identified.

Example 6: Selection of Antibody with Improved Affinity from the Libraries

If the binding affinity of an antibody derived from the libraries to c-Met was improved, the scFv gene sequence from that individual clone was analyzed. The obtained CDR sequences, shown in Table 2 below, were transformed into IgG. Among the clones listed below, 4 types of antibodies produced from L3-1, L3-2, L3-3, and L3-5 were selected and subsequent experiments were performed using these antibodies.

TABLE 2

| Name of clone | Library | CDR sequence | |
|---|---|---|---|
| H11-4 | CDR-H1 | PEYYMS | (SEQ ID NO: 22) |
| YC151 | CDR-H1 | PDYYMS | (SEQ ID NO: 23) |
| YC193 | CDR-H1 | SDYYMS | (SEQ ID NO: 24) |
| YC244 | CDR-H2 | RNNANGNT | (SEQ ID NO: 25) |
| YC321 | CDR-H2 | RNKVNGYT | (SEQ ID NO: 26) |
| YC354 | CDR-H3 | DNWLSY | (SEQ ID NO: 27) |
| YC374 | CDR-H3 | DNWLTY | (SEQ ID NO: 28) |
| L1-1 | CDR-L1 | KSSHSLLASGNQNNYLA | (SEQ ID NO: 29) |
| L1-3 | CDR-L1 | KSSRSLLSSGNHKNYLA | (SEQ ID NO: 30) |
| L1-4 | CDR-L1 | KSSKSLLASGNQNNYLA | (SEQ ID NO: 31) |
| L1-12 | CDR-L1 | KSSRSLLASGNQNNYLA | (SEQ ID NO: 32) |
| L1-22 | CDR-L1 | KSSHSLLASGNQNNYLA | (SEQ ID NO: 33) |
| L2-9 | CDR-L2 | WASKRVS | (SEQ ID NO: 34) |
| L2-12 | CDR-L2 | WGSTRVS | (SEQ ID NO: 35) |
| L2-16 | CDR-L2 | WGSTRVP | (SEQ ID NO: 36) |
| L3-1 | CDR-L3 | QQSYSRPYT | (SEQ ID NO: 13) |
| L3-2 | CDR-L3 | GQSYSRPLT | (SEQ ID NO: 14) |
| L3-3 | CDR-L3 | AQSYSHPFS | (SEQ ID NO: 15) |
| L3-5 | CDR-L3 | QQSYSRPFT | (SEQ ID NO: 16) |
| L3-32 | CDR-L3 | QQSYSKPFT | (SEQ ID NO: 37) |

Example 7: Transformation of Selected Antibodies to IgG

A polynucleotide encoding the heavy chain of the selected 4 types of antibodies consisted of 'EcoRI-signal sequence-VH-NheI-CH-XhoI' (SEQ ID NO: 38). The amino acids of the heavy chain were not modified after affinity was matured, so the heavy chain of the huAbF46 antibody was used. The hinge region was replaced with a U6-HC7 hinge region (SEQ ID NO: 57), not with the hinge region of human IgG1. A gene of the light chain was designed to have 'EcoRI-signal sequence-VL-BsiWI-CL-XhoI', and polynucleotides (SEQ ID NOS: 58 to 61) encoding light chain variable regions of the selected 4 types of antibodies were synthesized by Bioneer, Inc. Then, vectors for expression of the antibodies were constructed by cloning a DNA fragment (SEQ ID NO: 38) having the nucleic acid sequence corresponding to the heavy chain in a pOptiVEC™-TOPO TA Cloning Kit included in an OptiCHO™ Antibody Express Kit (Cat No. 12762-019) manufactured by Invitrogen and DNA fragments (a DNA fragment including L3-1-derived CDR-L3 (SEQ ID NO: 58), a DNA fragment including L3-2-derived CDR-L3 (SEQ ID NO: 39), a DNA fragment including L3-3-derived CDR-L3 (SEQ ID NO: 60), and a DNA fragment including L3-5-derived CDR-L3 (SEQ ID NO: 61)) corresponding to the light chain in a pcDNA™3.3-TOPO TA Cloning Kit (Cat No. 8300-01) by using a restriction enzyme, EcoRI (NEB, R0101S) and XhoI (NEB, R0146S), respectively.

The constructed vectors were amplified using a Qiagen Maxiprep kit (Cat No. 12662), and vectors including the heavy chain and vectors including the light chain were added to 293T cells ($2.5 \times 10^7$) at a ratio of about 4:1 (about 80 ug: 20 ug) with 360 ul of 2 M $CaCl_2$ and were transfected. Next, the mixture was cultured in a DMEM medium with 10% (w/v) FBS at 37° C. in 5% (v/v) $CO_2$ conditions for 5 hours, and then cultured in a DMEM medium without FBS at 37° C. in 5% (v/v) $CO_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was exchanged with a PBS buffer, and thus 4 types of antibodies having improved affinities (hereinafter, huAbF46-H4-A1, huAbF46-H4-A2, huAbF46-H4-A3, and huAbF46-H4-A5) were purified.

Example 8: Analysis of Binding Affinity of Selected Antibodies

Affinities of the 4 types of antibodies against c-Met antigen prepared in Example 7 were measured by using a Biacore (GE healthcare). About 80 to 110 RU of each antibody was immobilized on a CM5 chip, 9 different concentrations ranging from 0.39 nM to 100 nM of human c-Met protein, as an antigen, were injected at a rate of 30 ul/min to obtain $k_{on}$ values and $k_{off}$ values as shown in Table 3. Then, $K_D$ values were calculated based thereon. A binding affinity of huAbF46 to c-Met antigen was about 2.19 nM, and binding affinities of the four types of antibodies having improved affinities were in a range of 0.06 nM to 0.50 nM (Table 3). This indicates that affinities of the antibodies, which were improved in the form of scFv, were further improved by about 5 times to about 37 times after being transformed to IgG.

TABLE 3

| Antibody | $k_{on}$ (1/Ms) | $k_{off}$ (1/s) | $K_D$ (nM) |
|---|---|---|---|
| huAbF46 | $3.29 \times 10^5$ | $7.23 \times 10^{-4}$ | 2.19 |
| huAbF46-H4-A1 | $7.39 \times 10^5$ | $4.53 \times 10^{-5}$ | 0.06 |
| huAbF46-H4-A2 | $5.02 \times 10^5$ | $2.53 \times 10^{-4}$ | 0.50 |
| huAbF46-H4-A3 | $4.19 \times 10^5$ | $1.43 \times 10^{-4}$ | 0.34 |
| huAbF46-H4-A5 | $5.72 \times 10^5$ | $2.40 \times 10^{-4}$ | 0.42 |

Example 9: Analysis of In Vitro Biological Activity of Selected Antibodies Having Improved Affinities (1) BrdU Assay A BrdU assay was performed using the antibodies having improved affinities in order to evaluate safety of the antibodies. NCI-H441 (ATCC Cat. # HTB-174), human lung cancer cells, were suspended in a RPMI 1640 medium (Gibco) ($2\times10^5$ cell/ml) to prepare a suspension, and about 100 ul of the suspension was introduced to each well of a 96-well tissue culture plate (Corning, Lowell, Mass.). The suspension was incubated at 37° C. in 5% (v/v) $CO_2$ conditions for 24 hours, and then the medium was completely removed and replaced with a RPMI 1640 diluted with the antibody. After incubating the suspension at 37° C. in 5% (v/v) $CO_2$ conditions for 21 hours, 5-bromo-2'-deoxyuridine (BrdU) was added and the BrdU assay (Roche, Indianapolis, Ind.) was performed after a further 3 hours of incubation. After denaturing/fixing cells on the plate, an anti-BrdU antibody was added thereto and a substrate was added after an hour to measure a color reaction using an ELISA spectraMax reader (Molecular Devices, Sunnyvale, Calif.) at 370 nm. Media was used as a negative control, and an antibody 5D5 (ATCC Cat. # HB11895 separated from hybridoma cells and purified) well known as an agonist was used as a positive control.

Figure 2:
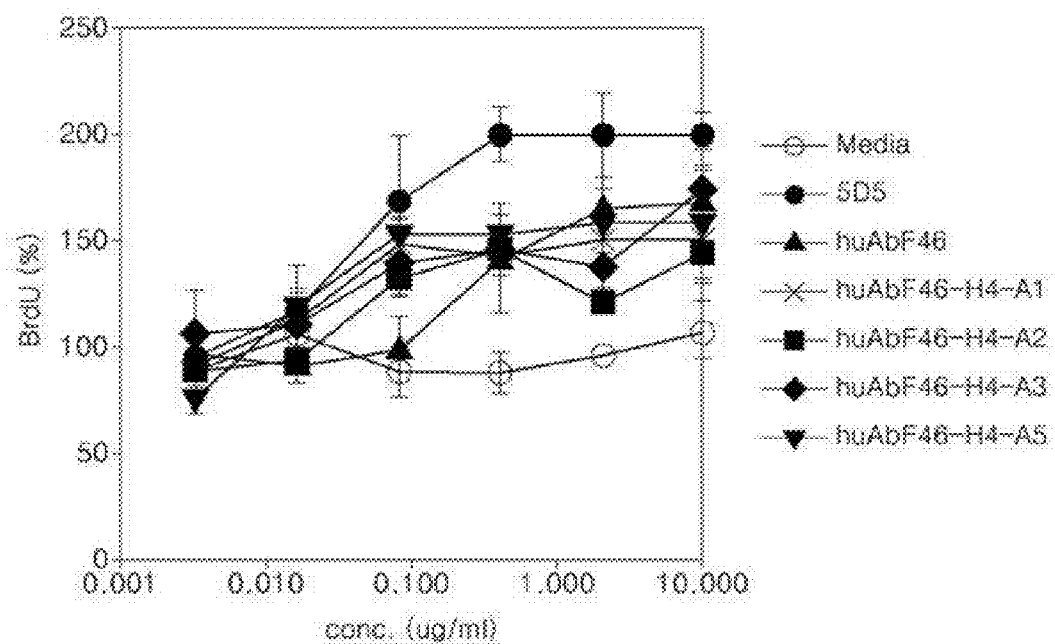
FIG. 2 is a graph of BrdU (%) plotted against antibody concentration, showing c-Met agonistic effect of huAbF46-H4-A1, huAbF46-H4-A2, huAbF46-H4-A3, and huAbF46-H4-A5 antibodies in a BrdU assay.

As a result, referring to FIG. 2, among the 4 types of antibodies having improved affinities, agonism side effects of 4 types were reduced. Thus, it was identified that safeties thereof were respectively improved by 25% (huAbF46-H4-A1), 28% (huAbF46-H4-A2), 13% (huAbF46-H4-A3), and 21% (huAbF46-H4-A5) at a concentration of 10 ug/ml.

(2) In Vitro Cell Proliferation Analysis

In order to identify anti-cancer effects of the 4 types of antibodies having improved affinities, as prepared in Example 5, in vitro cell proliferation analysis was performed using MKN45 gastric cancer cells on which c-Met is expressed (Japanese Cancer Research Bank, JCRB, Tokyo, Japan).

$1\times10^4$ MKN45 cells suspended in 50 ul of 5% (w/v) FBS/DMEM culture medium were introduced to each well of a 96-well plate. Then, the cells were either not treated or were treated with 50 ul of the 4 types of antibodies at a concentration of 0.008, 0.04, 0.2, or 1 ug/ml. After incubating for 72 hours, the number of cells was quantified by using a CellTiter-Glo Luminescent Cell Viability Assay Kit (Promega, G7570) with a leuminometer (PerkinElmer, 2104 Multilabel reader).

Figure 3:
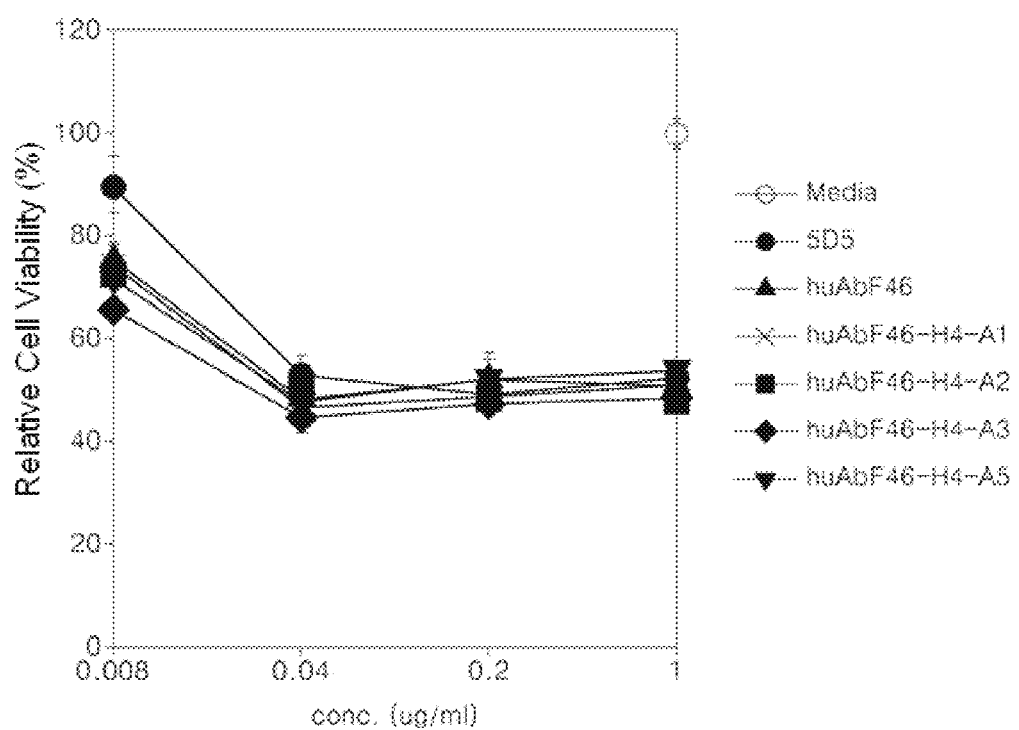
FIG. 3 is a graph of relative cell viability (%) plotted against antibody concentration, illustrating of the effect of huAbF46-H4-A1, huAbF46-H4-A2, huAbF46-H4-A3, and huAbF46-H4-A5 antibodies on in vitro cell proliferation.

As shown in FIG. 3, relative cell viability of the antibody (huAbF46) in which the affinity was not improved was 77% at the lowest concentration of 0.008 ug/ml, and relative cell viabilities of antibodies having improved affinities, i.e., huAbF46-H4-A1, huAbF46-H4-A2, and huAbF46-H4-A5 were respectively 74, 73, and 72% similar to each other. The relative cell viability of huAbF46-H4-A3, at 66%, was considerably decreased. In addition, at 0.04 ug/ml, where the effect on cell viability is maximized, relative cell viabilities of all of the 4 types of antibodies were equal or less than that of the antibody 5D5 (53%). Accordingly, as a result of improving affinity, efficiency and safety were significantly improved compared to the control.

(3) Akt Phosphorylation

Cellular processes regulated by Akt include cell proliferation, cell survival, cell size control, and response to nutrient availability, intermediary metabolism, angiogenesis, and tissue invasion. All these processes represent characteristics of cancer and many oncoproteins and tumor suppressors intersect in the Akt pathway, finely regulating cellular functions at the interface of signal transduction and classical metabolic regulation. Thus, as the content of phosphorylated Akt that is an active form increases, the activity of cancer cells increases. Here, the degree of inhibiting Akt phosphorylation by the 4 types of antibodies having improved affinities was evaluated.

To compare agonism of the 4 types of antibodies having improved affinities, as prepared in Example 5, Caki-1 cells (Korean Cell Line Bank) were used to confirm the degree of Akt phosphorylation. Mouse IgG was used as a negative control, and antibody 5D5 (a known agonist) was used as a positive control.

$2\times10^5$ cells/ml of Caki-1 cells were introduced to a 96-well plate, and after 24 hours, each of 5 ug/ml of the antibodies was treated in serum free medium for 30 minutes. Lysis of the cells treated with the antibodies was performed and the degree of Akt phosphorylation was measured using a PathScan phospho-AKT1 (Ser473) chemiluminescent Sandwich ELISA kit (Cell Signaling, cat. no #7134S).

Figure 4:
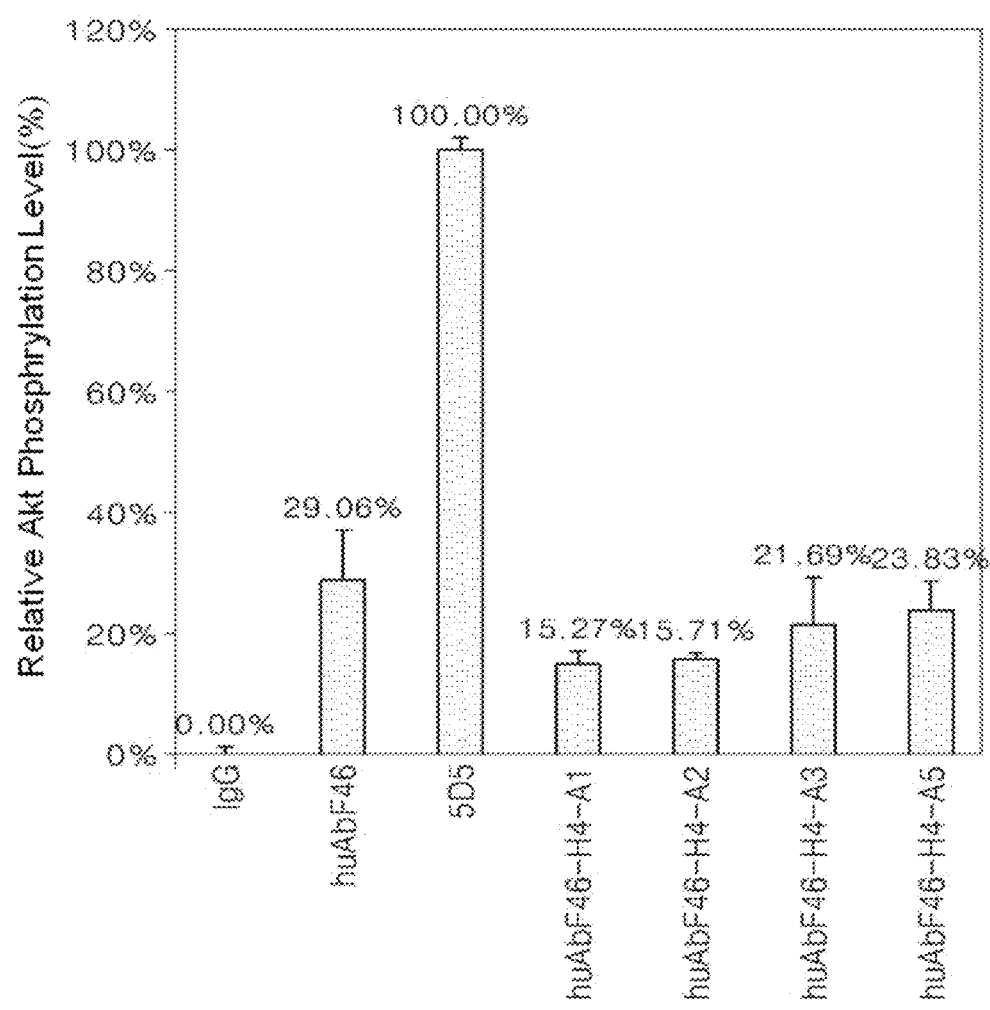
FIG. 4 is a graph of Akt phosphorylation (%) plotted against treatment antibody, which shows the degree of agonism of huAbF46-H4-A1, huAbF46-H4-A2, huAbF46-H4-A3, and huAbF46-H4-A5 antibodies.

As shown in FIG. 4, it was identified that the degree of inhibiting Akt phosphorylation of all of the 4 types of antibodies was improved. In particular, the degrees of Akt phosphorylation of huAbF46-H4-A1 and huAbF46-H4-A2 were 15.27% and 15.71%, respectively, which were about 49% of that (29.06%) before affinity was improved (huAbF46). Thus, it was identified that safety of the affinity maturated antibodies were considerably improved. In contrast, antibody 5D5 exhibits very high relative Akt phosphorylation level (100%), indicating that antibody 5D5 show a very high agionism and very low safety.

(4) Identification of Degree of Degradation of c-Met

In order to identify anti-cancer effects of the 4 types of antibodies having improved affinities, as prepared in Example 5, the degree of degradation of c-Met bound to the antibodies was evaluated. A relative total amount of c-Met was obtained by measuring the change in the total amount of c-Met after the antibody binds to c-Met to degrade c-Met via internalization, and thus the efficacy of the antibody was evaluated.

MKN45 cells ($2\times10^5$ cells/ml) and each of the antibodies (5 ug/ml) were simultaneously introduced to a 96-well plate and incubated for 24 hours. Then, lysis of the cells treated with antibodies was performed and the change in the total amount of c-Met was measured using a Human total HGF R/c-Met ELISA KIT (R&D systems, DYC358) and analyzed.

Figure 5:
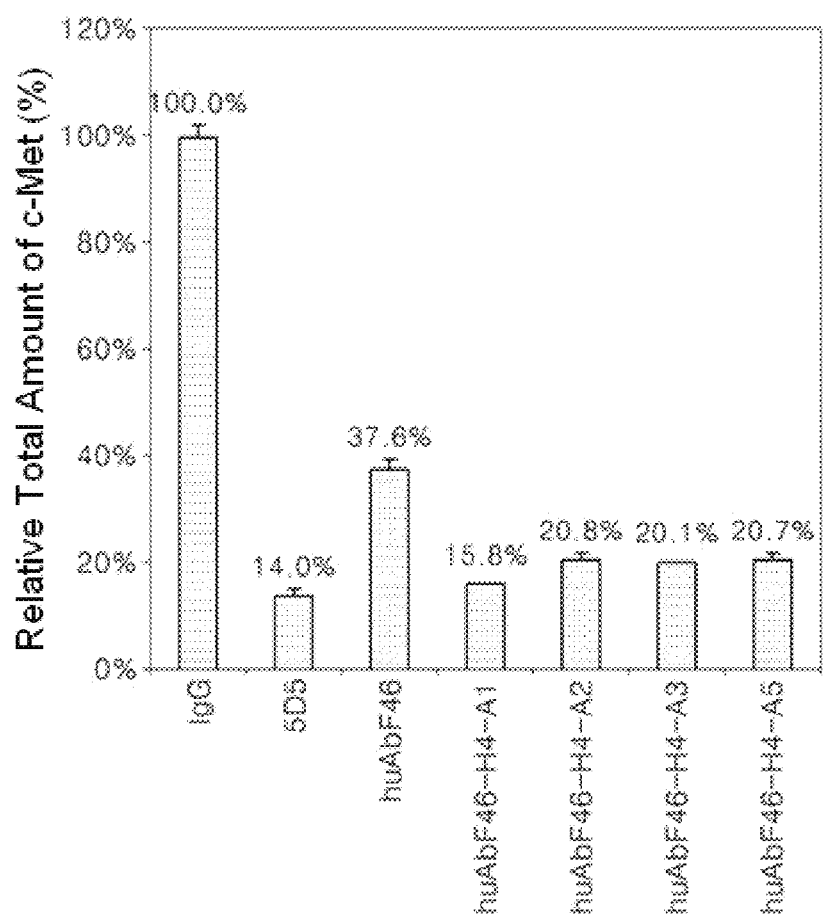
FIG. 5 is a graph illustrating anti-cancer effects of huAbF46-H4-A1, huAbF46-H4-A2, huAbF46-H4-A3, and huAbF46-H4-A5 antibodies as measured by the degree of degradation of c-Met.

As a result, referring to FIG. 5, it was identified that the degree of degradation of c-Met was improved when cells were treated with the 4 types of antibodies having improved affinities compared to cells treated with the huAbF46 antibody. The degree of degradation of c-Met in cells treated with huAbF46-H4-A1 was increased by about 37% compared to cells treated with huAbF46. The degrees of degradation of c-Met in cells treated with huAbF46-H4-A2, huAbF46-H4-A3, and huAbF46-H4-A5 were increased by about 28% compared to cells treated with huAbF46. As shown in FIGS. 4 and 5, the affinity maturated antibodies show equal or higher degree of degradation of c-Met as well as very higher safety compared to those of antibody 5D5.

Example 10: Analysis of In Vivo Biological Activity of Selected Antibodies Having Improved Affinities In order to identify anti-cancer effects of the 4 types of antibodies having improved affinities, as prepared in Example 5, a decrease in the size of tumor cells in a brain cancer or gastric cancer mouse xenograft model transplanted with U87MG brain cancer cells (Korean Cell Line Bank) or MKN45 gastric cancer cells (Japanese Cancer Research Bank, JCRB, Tokyo, Japan) was observed when the antibodies having improved affinities were administered thereto in vivo.

For MKN45 model (FIG. 6A), $5 \times 10^6$ MKN45 cells (100 uL) were administered via subcutaneous injection to 6 week-old male BALB/C nude mice (SLAC Laboratoris, Shanghai, China). For U87MG model (FIG. 6B), $2.5 \times 10^6$ U87MG cells were administered. One wee after the tumor inoculation, the mice were randomized into Vehicle (PBS) or huAbF46-H4-A1 treatment groups at a various doses (0.2 mg/kg-10 mg/kg). Each group consisted of 15 mice. For MKN45 model, each treatment was given once a week via intravenous route, for total of 4 doses. For U87MG model, the treatment was given every 10 days for total of 3 doses.

Figure 6A:
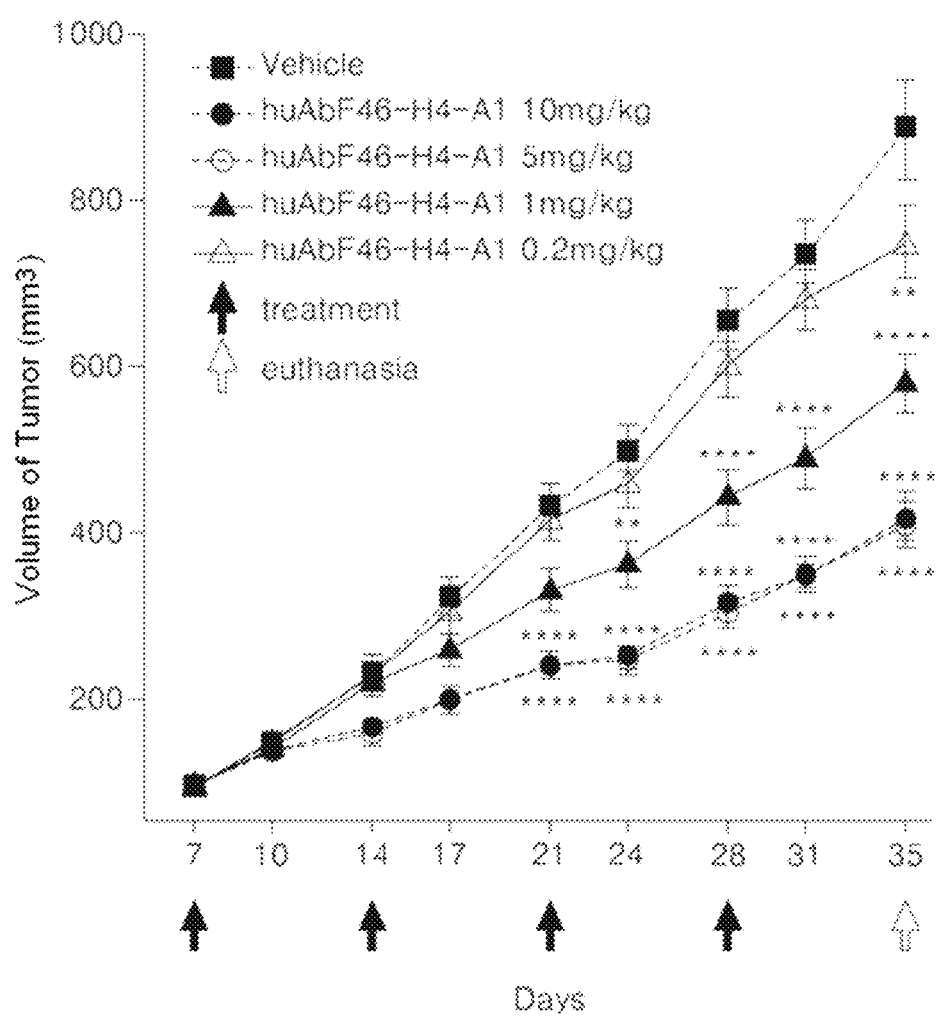
FIGS. 6A and 6B are graphs of tumor volume plotted against time (days), showing in vivo anti-cancer effects of various concentrations of huAbF46-H4-A1 antibody in U87MG brain cancer mouse xenograft model or MKN45 gastric cancer mouse xenograft model.
Figure 6B:
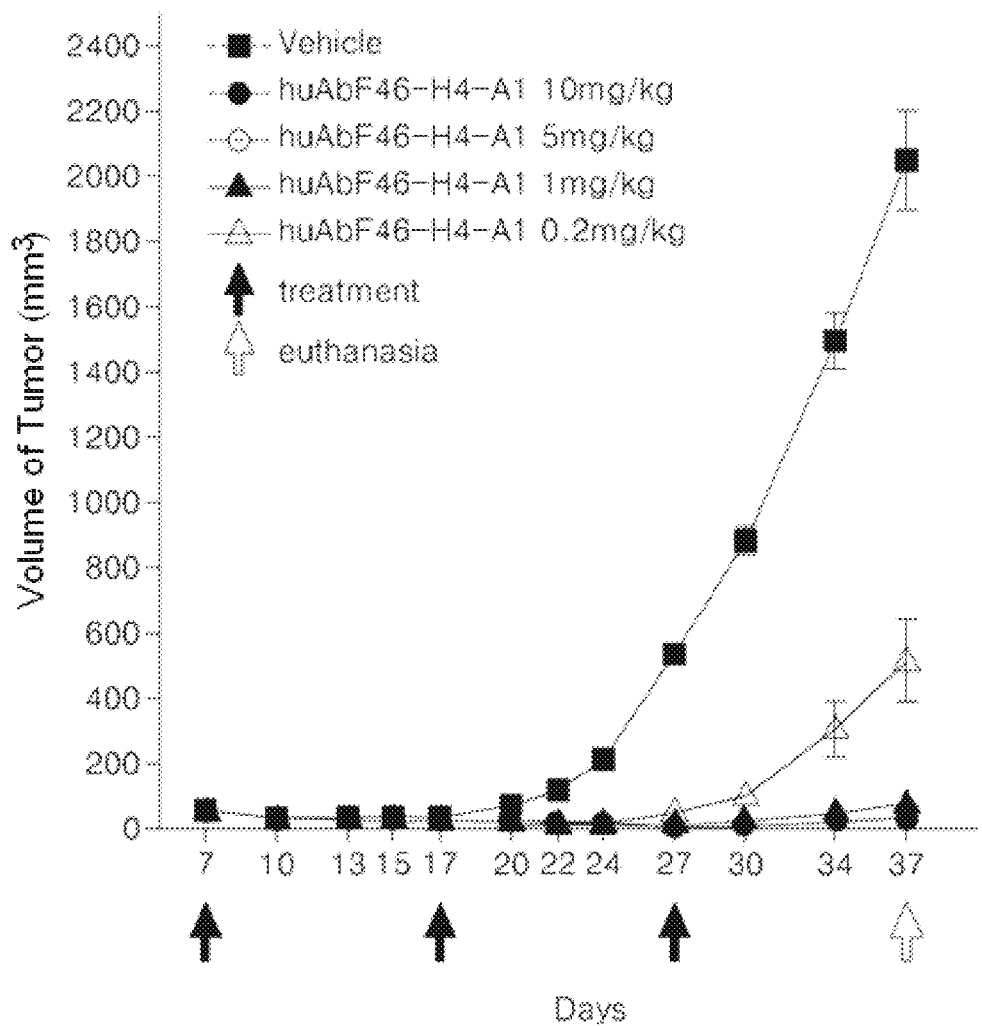

Referring to FIGS. 6A and 6B, in both the U87MG brain cancer and the MKN45 gastric mouse cancer models, dose-dependent tumor growth inhibiting effects of huAbF46-H4-A1 were identified.

Example 11: Preparation of huAbF46-H4-A1 Having Replaced Constant Region and/or Hinge Region Among the selected 4 types of antibodies, huAbF46-H4-A1 was determined to have the highest binding affinity to c-Met and the lowest degrees of Akt phosphorylation and c-Met differentiation. The hinge region, or the constant region and hinge region, of huAbF46-H4-A1 was replaced.

An antibody including a heavy chain that includes a heavy chain variable region of huAbF46-H4-A1, a U6-HC7 hinge, and a human IgG1 constant region, and a light chain that includes a light chain variable region of huAbF46-H4-A1 and a human kappa constant region was named huAbF46-H4-A1 (U6-HC7), an antibody including a heavy chain that includes a heavy chain variable region of huAbF46-H4-A1, a human IgG2 hinge, and a human IgG1 constant region and a light chain that includes a light chain variable region of huAbF46-H4-A1 and a human kappa constant region was named huAbF46-H4-A1 (IgG2 hinge), and an antibody including a heavy chain that includes a heavy chain variable region of huAbF46-H4-A1, a human IgG2 hinge, and a human IgG2 constant region and a light chain that includes a light chain variable region of huAbF46-H4-A1 and a human kappa constant region was named huAbF46-H4-A1 (IgG2 Fc). In addition, in order to increase productivity of the 3 types of antibodies all histidine was replaced with tyrosine at position 36 in the light chain including the human kappa constant region.

In order to prepare the 3 types of antibodies, a polynucleotide (SEQ ID NO: 63) encoding a polypeptide (SEQ ID NO: 62) including the heavy chain variable region of huAbF46-H4-A1, the U6-HC7 hinge region, and the human IgG1 constant region, a polynucleotide (SEQ ID NO: 65) encoding a polynucleotide (SEQ ID NO: 65) including the heavy chain variable region of huAbF46-H4-A1, the human IgG2 hinge region, and the human IgG1 constant region, a polynucleotide (SEQ ID NO: 67) encoding a polypeptide (SEQ ID NO: 66) including the heavy chain variable region of huAbF46-H4-A1, the human IgG2 hinge region, and the human IgG2 constant region, and a polynucleotide (SEQ ID NO: 69) encoding a polypeptide (SEQ ID NO: 68) including the light chain variable region of huAbF46-H4-A1 in which histidine is replaced with tyrosine at position 36 and the human kappa constant region were synthesized by Bioneer, Inc. Then, vectors for expression of the antibodies were constructed by cloning a DNA fragment having the nucleic acid sequence corresponding to the heavy chain in a pOptiVEC™-TOPO TA Cloning Kit included in an OptiCHO™ Antibody Express Kit (Cat No. 12762-019) manufactured by Invitrogen, and a DNA fragment having the nucleic acid sequence corresponding to the light chain in a pcDNA™3.3-TOPO TA Cloning Kit (Cat No. 8300-01).

The constructed vectors were amplified using a Qiagen Maxiprep kit (Cat No. 12662), and vectors including the heavy chain and vectors including the light chain were added to 293T cells ($2.5 \times 10^7$) at a ratio of about 4:1 (about 80 ug:20 ug) with 360 ul of 2 M $CaCl_2$ and were transfected. Then, the mixture was cultured in a DMEM medium added with 10% (w/v) FBS at 37° C. in 5% (v/v) $CO_2$ conditions for 5 hours, and then cultured in a DMEM medium without FBS at 37° C. in 5% (v/v) $CO_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was exchanged with a PBS buffer, and 3 types of antibodies (huAbF46-H4-A1 (U6-HC7), huAbF46-H4-A1 (IgG2 hinge), and huAbF46-H4-A1 (IgG2 Fc)) were purified.

In addition, another light chain (SEQ ID NO: 73) was prepared by replacing the amino acid residue, serine, at the position 27e (according to kabat numbering) of the light chain variable region of huAbF46-H4-A1 with tryptophan. Then, an antibody including the prepared light chain and the heavy chain of huAbF46-H4-A1 (IgG2 Fc) was prepared as described above, and named as L3-11Y. The binding affinity of the L3-11Y antibody was measured according to the method described in Example 8, and the measured binding affinity ($K_D$ (nM)) was less than 0.01 (<0.01).

Example 12: Analysis of In Vitro Biological Activity of huAbF46-H4-A1 Having Replaced Constant Region and/or Hinge Region (1) In Vitro Cell Proliferation Analysis In order to identify anti-cancer effects of the three types of antibodies prepared in Example 11, in vitro cell proliferation analysis was performed using MKN45 gastric cancer cells having c-Met on the cell membrane (Japanese Cancer Research Bank, JCRB, Tokyo, Japan).

$1 \times 10^4$ MKN45 cells suspended in 50 ul of 5% (w/v) FBS/DMEM culture medium were introduced to each well of a 96-well plate. Then, the cells were either not treated or were treated with 50 ul of the 3 types of antibodies at a concentration of 0.008, 0.04, 0.2, or 1 ug/ml. After incubating for 72 hours, the number of cells was quantified by using a CellTiter-Glo Luminescent Cell Viability Assay Kit (Promega, G7570) with a leuminometer (PerkinElmer, 2104 Multilabel reader).

Figure 7:
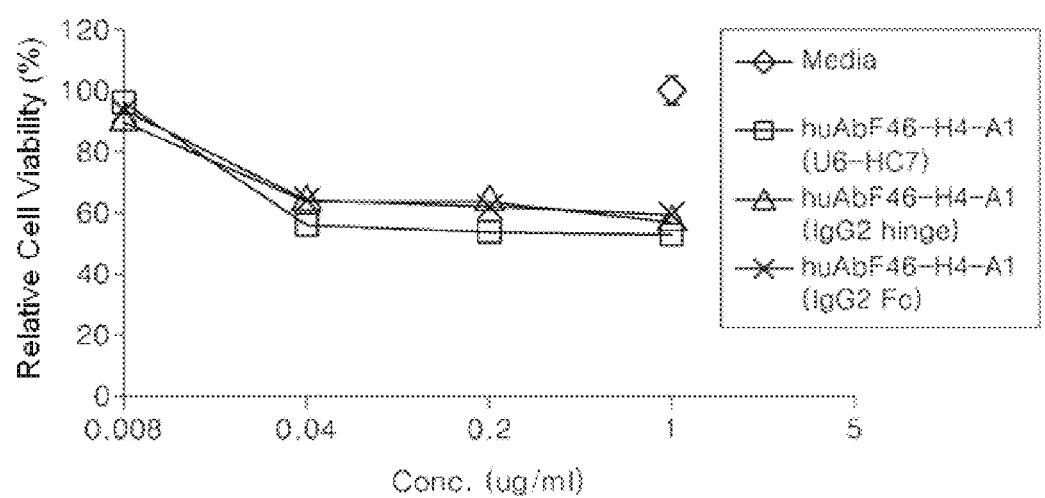
FIG. 7 is a graph of relative cell viability (%) plotted against antibody concentration, showing the effect of huAbF46-H4-A1 (U6-HC7), huAbF46-H4-A1 (IgG2 hinge), and huAbF46-H4-A1 (IgG2 Fc) antibodies on in vitro cell proliferation.

As shown in FIG. 7, when the 3 types of antibodies, huAbF46-H4-A1 (U6-HC7), huAbF46-H4-A1 (IgG2 hinge), and huAbF46-H4-A1 (IgG2 Fc), were treated at a concentration of 0.04 ug/ml or less, the relative cell viability was about 60%.

(2) Akt Phosphorylation

To compare agonism of the 3 types of antibodies having improved affinities, as prepared in Example 11, Caki-1 cells (Korean Cell Line Bank) were used to confirm the degree of Akt phosphorylation. Mouse IgG was used as a negative control, and a 5D5 antibody (a known agonist) was used as a positive control.

$2 \times 10^5$ cells/ml of Caki-1 cells were introduced to a 96-well plate, and after 24 hours, each of 5 ug/ml of the antibodies was treated in serum free medium for 30 minutes. Lysis of the cells treated with antibodies was performed and a degree of Akt phosphorylation inhibition was measured using a PathScan phospho-AKT1 (Ser473) a chemiluminescent Sandwich ELISA kit (Cell Signaling, cat. no #7134S).

Figure 8A:
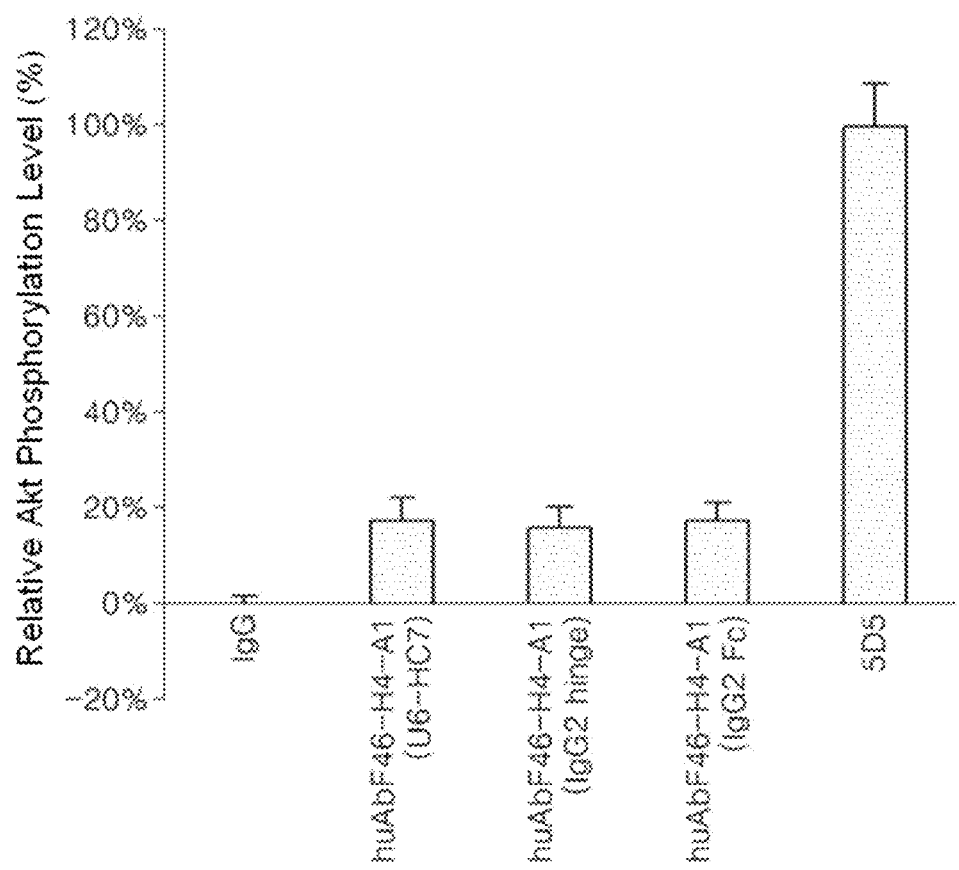
FIGS. 8A and 8B are graphs of Akt phosphorylation (%) plotted against treatment antibody, which shows the degree of agonism of the antibodies.
Figure 8B:
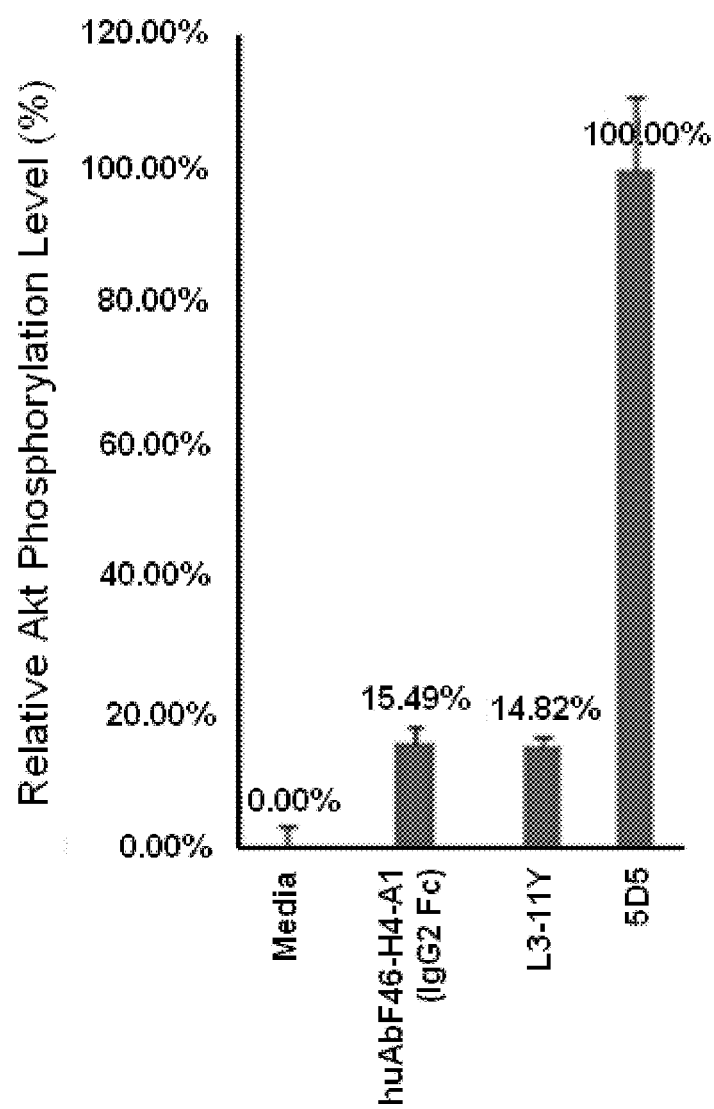

The obtained results are shown in FIG. 8A. As shown in FIG. 8A, the degrees of inhibiting Akt phosphorylation of all of the 3 types of antibodies were 18% or less. Thus, it was identified that safety was considerably improved.

In addition, the degrees of Akt phosphorylation inhibition of huAbF46-H4-A1 (IgG2 Fc) and L3-11Y were also measured according the above method. The obtained results are shown in FIG. 8B. As shown in FIG. 8B, L3-11Y exhibits an equal or higher activity of Akt phosphorylation inhibition compared to that of huAbF46-H4-A1 (IgG2 Fc).

(3) Identification of Degree of Degradation of c-Met

In order to identify anti-cancer effects of the 3 types of antibodies having improved affinities, as prepared in Example 11, the degree of degradation of c-Met bound to the antibody was evaluated. MKN45 cells ($2 \times 10^5$ cells/ml) and each of the antibodies (5 ug/ml) were simultaneously introduced to a 96-well plate and incubated for 24 hours. Then, lysis of the cells treated with antibodies was performed and a change of the total amount of c-Met was measured using a Human total HGF R/c-Met ELISA KIT (R&D systems, DYC358) and analyzed.

Figure 9A:
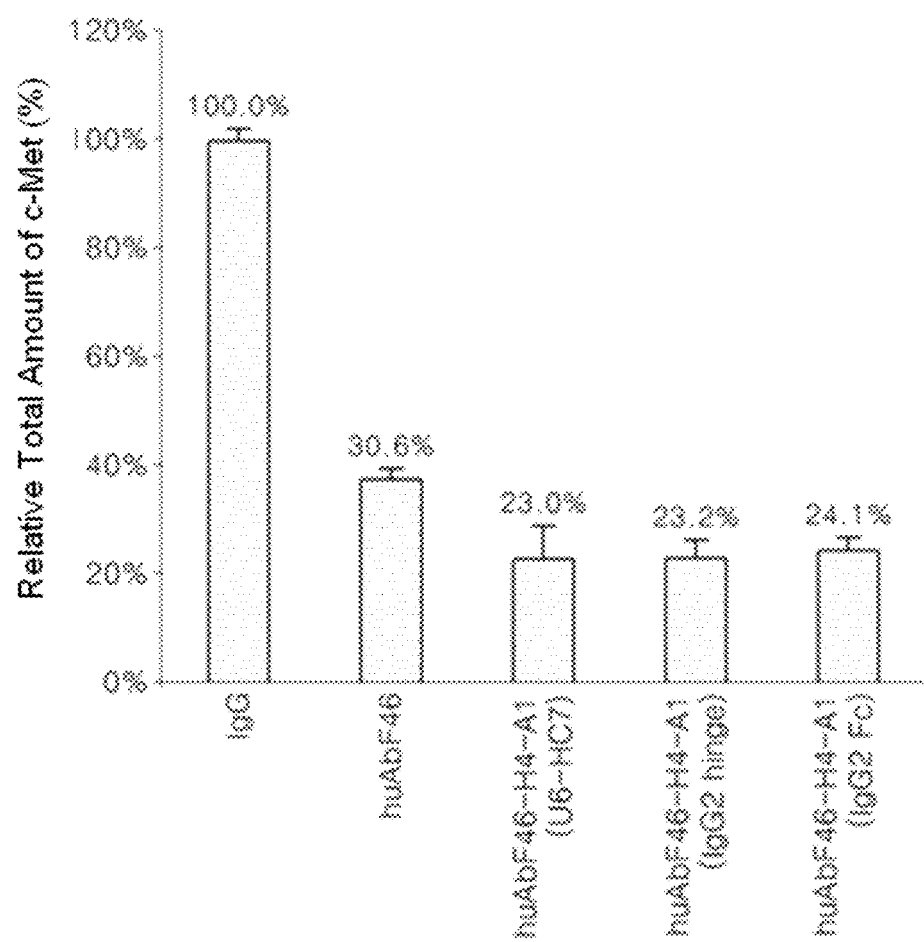
FIGS. 9A and 9B are graphs illustrating anti-cancer effects of antibodies as measured by degree of degradation of c-Met.
Figure 9B:
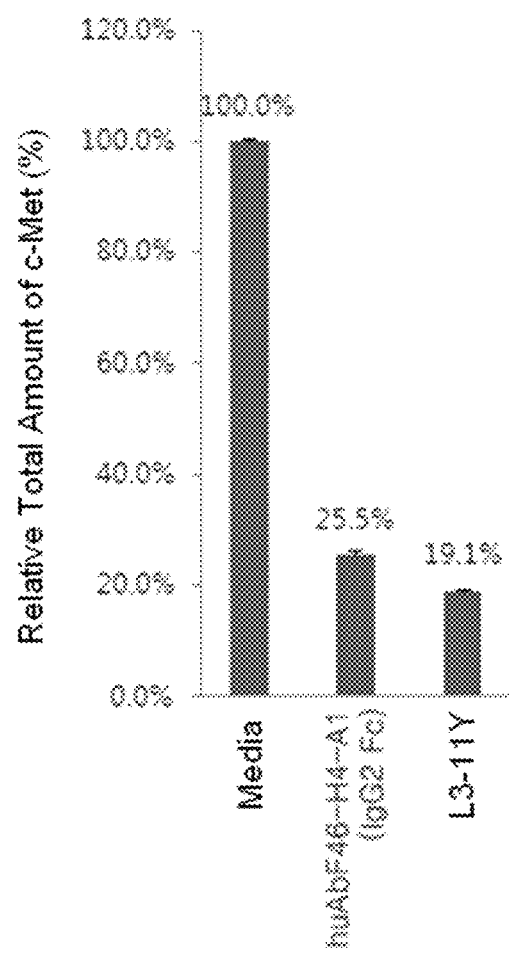

The obtained results are shown in FIG. 9A. As shown in FIG. 9A, it was identified that the degree of degradation of c-Met was improved in cells treated with the 3 types of antibodies having improved affinities compared to cells treated with the huAbF46 antibody.

In addition, the degrees of c-Met degradation of huAbF46-H4-A1 (IgG2 Fc) and L3-11Y were also measured according the above method. The obtained results are shown in FIG. 9B. As shown in FIG. 9B, L3-11Y exhibits an approximately equal activity of c-Met degradation compared to that of huAbF46-H4-A1 (IgG2 Fc).

Example 13: Analysis of In Vivo Biological Activity of huAbF46-H4-A1 Having Replaced Constant Region and/or Hinge Region In order to identify anti-cancer effects of the 3 types of antibodies having improved affinities, as prepared in Example 11, a decrease in the size of tumor cells in a brain cancer or gastric cancer mouse xenograft model transplanted with U87MG brain cancer cells (Korean Cell Line Bank) or MKN45 gastric cancer cells (Japanese Cancer Research Bank, JCRB, Tokyo, Japan) was observed when the antibodies having improved affinities were administered in vivo.

Figure 10A:
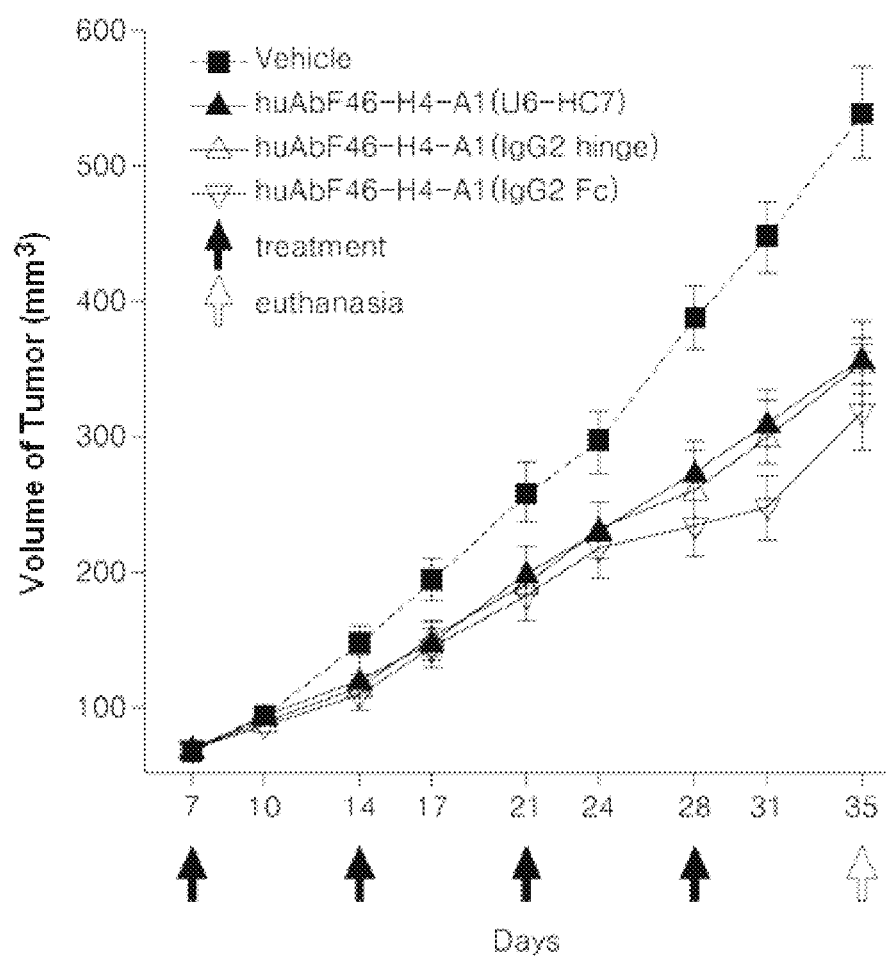
FIGS. 10A and 10B are graphs of tumor volume plotted against time (days), showing in vivo anti-cancer effects of huAbF46-H4-A1 (U6-HC7), huAbF46-H4-A1 (IgG2 hinge), and huAbF46-H4-A1 (IgG2 Fc) antibodies in U87MG brain cancer mouse xenograft model or MKN45 gastric cancer mouse xenograft model.
Figure 10B:
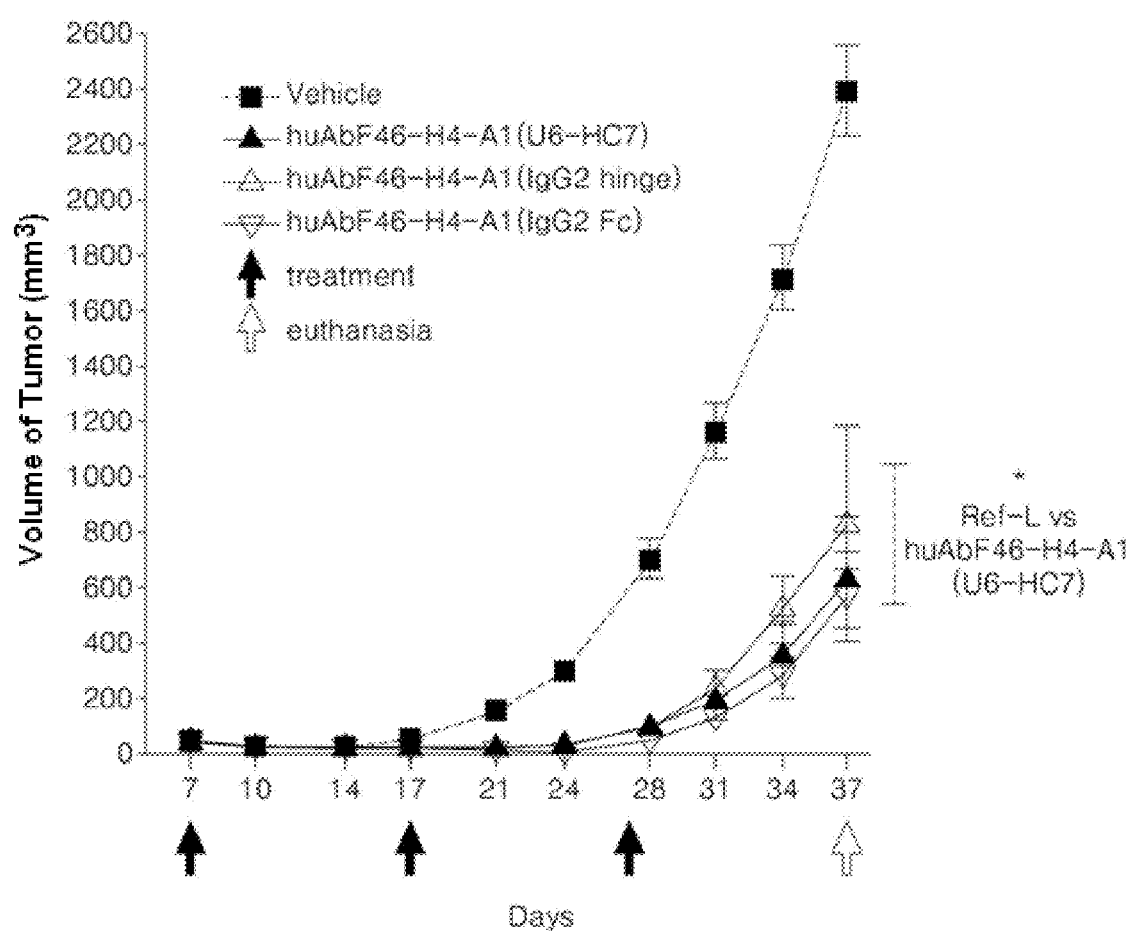

For MKN45 model (FIG. 10A), $5 \times 10^6$ MKN45 cells (100 uL) were administered via subcutaneous injection to 6 week-old male BALB/C nude mice (SLAC Laboratoris, Shanghai, China). For U87MG model (FIG. 10B), $2.5 \times 10^6$ U87MG cells were administered. One week after the tumor inoculation, the mice were randomized into Vehicle (PBS) group or 3 different antibody treatment groups (huAbF46-H4-A1 U6-HC7, IgG2 hinge, or IgG2 Fc). Each group consisted of 15 mice. For MKN45 model, each treatment was given at 1 mg/kg once a week via intravenous route, for total of 4 doses. For U87MG model, the treatment was given at 0.2 mg/kg every 10 days for total of 3 doses.

In both of the MKN45 gastric cancer (FIG. 10A) or U87MG brain cancer mouse cancer models (FIG. 10B), the three types of antibodies showed comparable levels of tumor growth inhibiting effect.

Example 14: Anti-Migration Activity of huAbF46-H4-A1 (IgG2 Fc) (In Vitro)

Cell migration inhibition ratio of huAbF46-H4-A1 (IgG2 Fc) was analyzed by RTCA (Real Time Cell Analyzer). RTCA is a labeling-free cell-based assay system integrating microelectronics and cell biology, suitable for uninterrupted monitoring of biological processes of living cells.

NCI-H441 cells (ATCC Cat. # HTB-174), SNU-638 cells (Korean Cell Line Bank (KCLB), Cat. #00638), and Capan-2 cells (ATCC Cat. # HTB-80) were respectively plated at a density of $1 \times 10^5$ cells per well in 130 μL of serum-free RPMI 1640 medium onto upper chamber of a 16-well CIM plate (Roche). To test whether huAbF46-H4-A1 (IgG2 Fc) induces cell migration inhibition, 10 μg/mL of huAbF46-H4-A1 (IgG2 Fc) were treated in lower chamber in the absence or presence of HGF (200 ng/mL) in FBS 10% (v/v) RPMI 1640 medium (total volume of 160 μL).

During incubation at 37° C. with 5% $CO_2$, the cell Index (CI) was recorded in real time. The obtained results were summarized in Table 4.

TABLE 4

| Cell Line | H441 | | SNU-638 | | Capan-2 | |
|---|---|---|---|---|---|---|
| Conc. (μg/mL) | 10 | | 10 | | 10 | |
| Time point (hr) | 20 | | 48 | | 35 | |
| HGF (200 ng/mL) | (+) | (−) | (+) | (−) | (+) | (−) |
| Relative inhibition rate (%) | 69.8 | N/A | 73.4 | 10.7 | 86.2 | Not tested | cf. N/A: cells did not migrate in the absence of hepatocyte growth factor (HGF)

huAbF46-H4-A1 (IgG2 Fc) showed dose-dependent anti-migration activity, using Real Time Cell Analyzer (RTCA), in 3 cancer cell lines. The relative migration inhibition rate shown in Table 4 was calculated at a specific time-point when the inhibition level was most significant per cell line. The 'N/A' mark in Table 4 means that cells did not migrate in the absence of hepatocyte growth factor (HGF). Therefore, the inhibitory level of huAbF46-H4-A1 (IgG2 Fc) could not be measured under these conditions.

Example 15: Anti-Migration Activity of huAbF46-H4-A1 (IgG2 Fc) (In Vivo)

For the MKN45 orthotopic xenograft experiment, human gastric cancer MKN45 cells (Japanese Cancer Research Bank, JCRB, Tokyo, Japan) were inoculated into donor BALB/C nude mice. When the tumor size reached the size of 600-800 mm3, the donor mice were euthanized, and the tumor was excised through sterile surgical procedure. The tumors were cut into fragments the size of $1 \times 1 \times 1$ mm and implanted into the wall of great gastric curvature of recipient mice through sterile surgery under isoflurane anesthesia. 7 days after the surgery, recipient mice with orthotopic tumors were randomized into groups according to body weight and dosing was commenced. huAbF46-H4-A1 (IgG2 Fc) was injected into a vein once a week for 9 weeks. At the end of the in vivo study, orthotopic tumor weight was recorded and metastasis to the other organ was checked by macroscopic examination.

The number of metastasis and adhesion lesion in MKN45 orthotopic xenograft are shown in Table 5:

TABLE 5

| Groups | Number of metastasis lesion |
|---|---|
| PBS | 4 |
| 5-FU | 0 |
| huAbF46-H4-A1 (IgG2 Fc) 10 mg/kg | 0 |
| huAbF46-H4-A1 (IgG2 Fc) 5 mg/kg | 0 |
| huAbF46-H4-A1 (IgG2 Fc) 1 mg/kg | 1 |

As shown in Table 5, metastasis from stomach to the other organ, such as liver and kidney was found 4 of 9 mice in the vehicle group, whereas occurrence of metastasis decreased with huAbF46-H4-A1 (IgG2 Fc) treatment in a dose-dependent manner. In conclusion, huAbF46-H4-A1 (IgG2 Fc) showed an anti-tumor efficacy in MKN45 orthotopic xenograft in dose dependent manner and inhibited the occurrence of metastasis to the other organ.

Example 16: Anticancer Effect of huAbF46-H4-A1 (IgG2 Fc) on EBC1 Cell Line 16.1. Experiment 1

The effect of huAbF46-H4-A1 (IgG2 Fc) on the growth of human lung cancer cell line EBC-1 subcutaneous xenografts in BALB/C nude mice was evaluated. 5 million EBC-1 cells were injected s.c. Four days after inoculation, dosing commenced in treatment groups. For the xenograft experiment, EBC-1 cells (JCRB, Japan) were subcutaneously inoculated into donor BALB/C nude mice. Each group consisted of 15 animals. Vehicle control (PBS) and huAbF46-H4-A1 (IgG2 Fc) (0.03, 0.1, 0.3, 1, 3 or 10 mg/kg) treatment groups were dosed i.v. q.w.×4 injections. Tumor volumes and body weights were measured two to three times a week for total study period about 4 weeks. The tumor volume (V) was calculated as follows: V (mm3)=[long axis length (mm)× (short axis length (mm))$^2$]/2.

Figure 11:
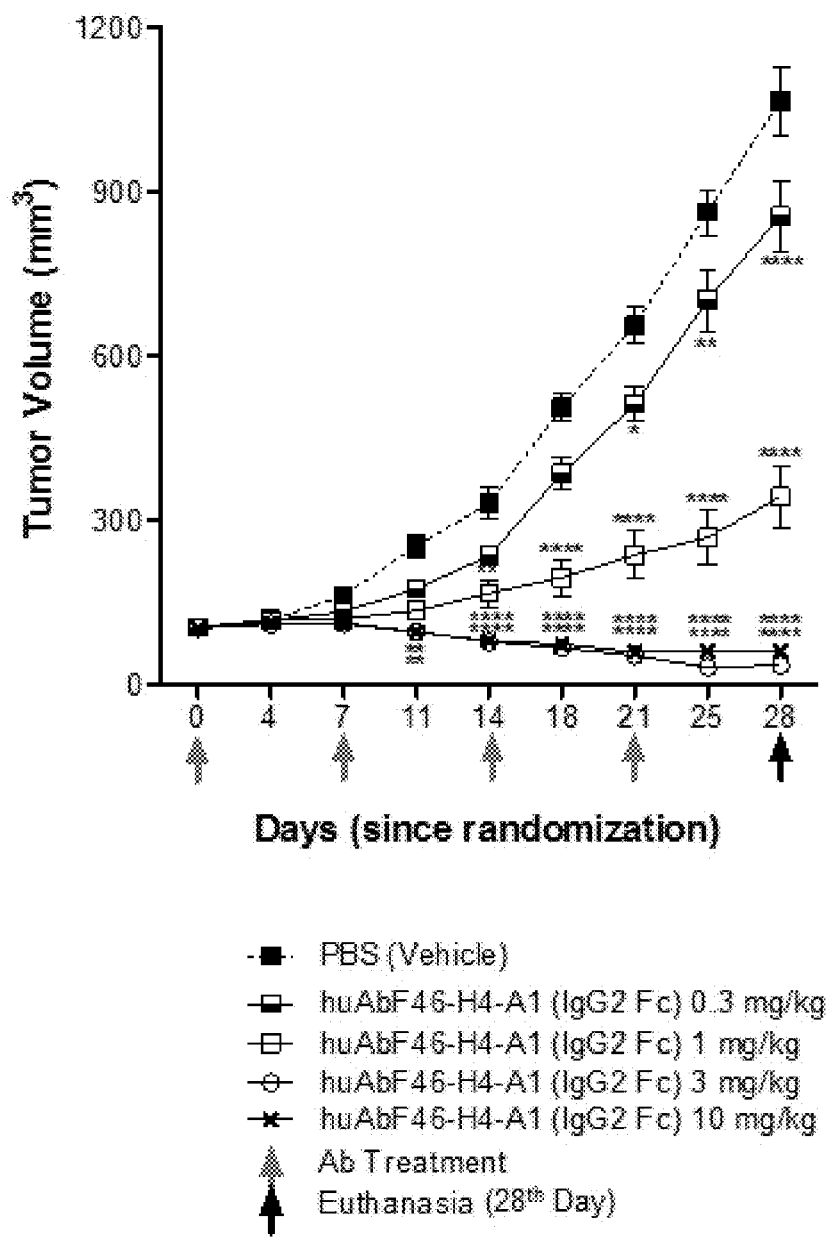
FIG. 11 is a graph of tumor volume plotted against time (days), showing dose-dependent in vivo anti-cancer effect of huAbF46-H4-A1 (IgG2 Fc) in EBC1 lung cancer mouse xenograft model.

The obtained results (tunor volumes) are shown in FIG. 11. In FIG. 11, tumor volumes were measured on indicated days are plotted (mean and s.e.m.) for treatment groups (huAbF46-H4-A1 (IgG2 Fc)) and PBS (negative control) group. Asterisks (*) represent P-values versus vehicle group according to repeated measures ANOVA on each indicated day (*P<0.05, P<0.01, *P<0.001, ****P<0.0001). As shown in FIG. 11, the tumor volumes are significantly reduced by treatment of huAbF46-H4-A1 (IgG2 Fc) in dose-dependent manner.

16.2. Experiment 2

To study the effect of anti-c-Met antibodies on tumor growth in vivo, tumor xenograft studies were performed using 5-6 weeks old male BALB/c Nude mice. Mice were acclimated for at least a week before they received tumor inoculation. 5 million EBC1 cells (JCRB, Japan) in 200 μl of serum-free media/matrigel (50:50 v/v) were injected subcutaneously into the right flank region of the mice under anesthesia by 1-2% isoflurane. After 7 days, when the average tumor size was close to 100-200 mm$^3$, mice were randomized into the following treatment groups: 5D5 (5 mg/kg I.V. once a week), huAbF46-H4-A1 (IgG2 Fc) (5 mg/kg I.V. once a week), and vehicle (PBS 0.2 ml I.V. once a week). Each treatment group consisted of 15 mice. Tumor volumes and body weights were measured two to three times a week for total study period about 4 weeks. The tumor volume (V) was calculated as follows: V (mm$^3$)={long axis length (mm)×(short axis length (mm))$^2$}/2. Tumor growth inhibition was calculated as follows: 100−100*(ΔTV in huAbF46-H4-A1 (IgG2 Fc) group)/(ΔTV in Vehicle group), where ΔTV=TV(end)−TV(d0).

Figure 12:
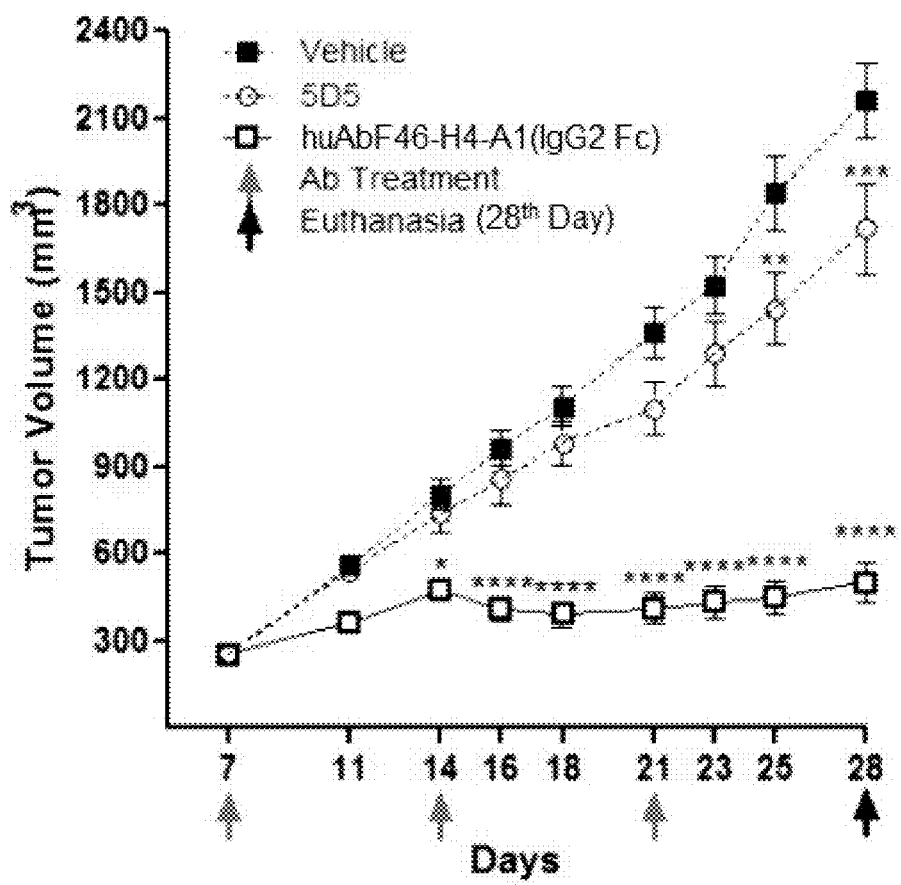
FIG. 12 is a graph of tumor volume plotted against time (days), showing another example of in vivo anti-cancer effect of huAbF46-H4-A1 (IgG2 Fc) in EBC1 lung cancer mouse xenograft model.

The obtained results are shown in FIG. 12. In FIG. 12, tumor volumes measured on indicated days are plotted (mean and SEM) for two treatment groups (5D5 and huAbF46-H4-A1 (IgG2 Fc)) and vehicle (negative control) group. Asterisks (*) represent p values versus vehicle group according to repeated measures ANOVA (*: p<0.05, : p<0.01, *: p<0.001, ****: p<0.0001). As shown in FIG. 12, huAbF46-H4-A1 (IgG2 Fc) demonstrated a strong inhibition of tumor growth, resulting in the tumor growth inhibition of 77% in EBC1 model. In comparison, 5D5 treatment resulted in much less tumor growth inhibition.

Example 17: Anticancer Effect of huAbF46-H4-A1 (IgG2 Fc) on MHCC97H Cell Line

The antitumor activity of huAbF46-H4-A1 (IgG2 Fc) was evaluated in a BALB/C nude mouse MHCC97H (human liver cancer cell line) xenograft model (referring to Example 16.2). Approximately 3 million MHCC97H cells in 100 μL of serum-free media were injected via s.c. to each of the 140 mice under anesthesia by 1-2% isoflurane. Ten days after subcutaneous inoculation with MHCC97H tumor cells, dosing commenced in the following treatment groups: 0 (PBS vehicle), 0.2, 1, 5 or 10 mg/kg huAbF46-H4-A1 (IgG2 Fc) i.v., q.w.×4 weeks; 30 mg/kg sorafenib p.o., q.d.×4 weeks (positive control). Each group consisted of 15 mice. Tumor volumes and body weights were measured two to three times a week for total study period about 4 weeks. The tumor volume (V) was calculated as follows: V (mm$^3$)={long axis length (mm)×(short axis length (mm))$^2$}/2.

Figure 13:
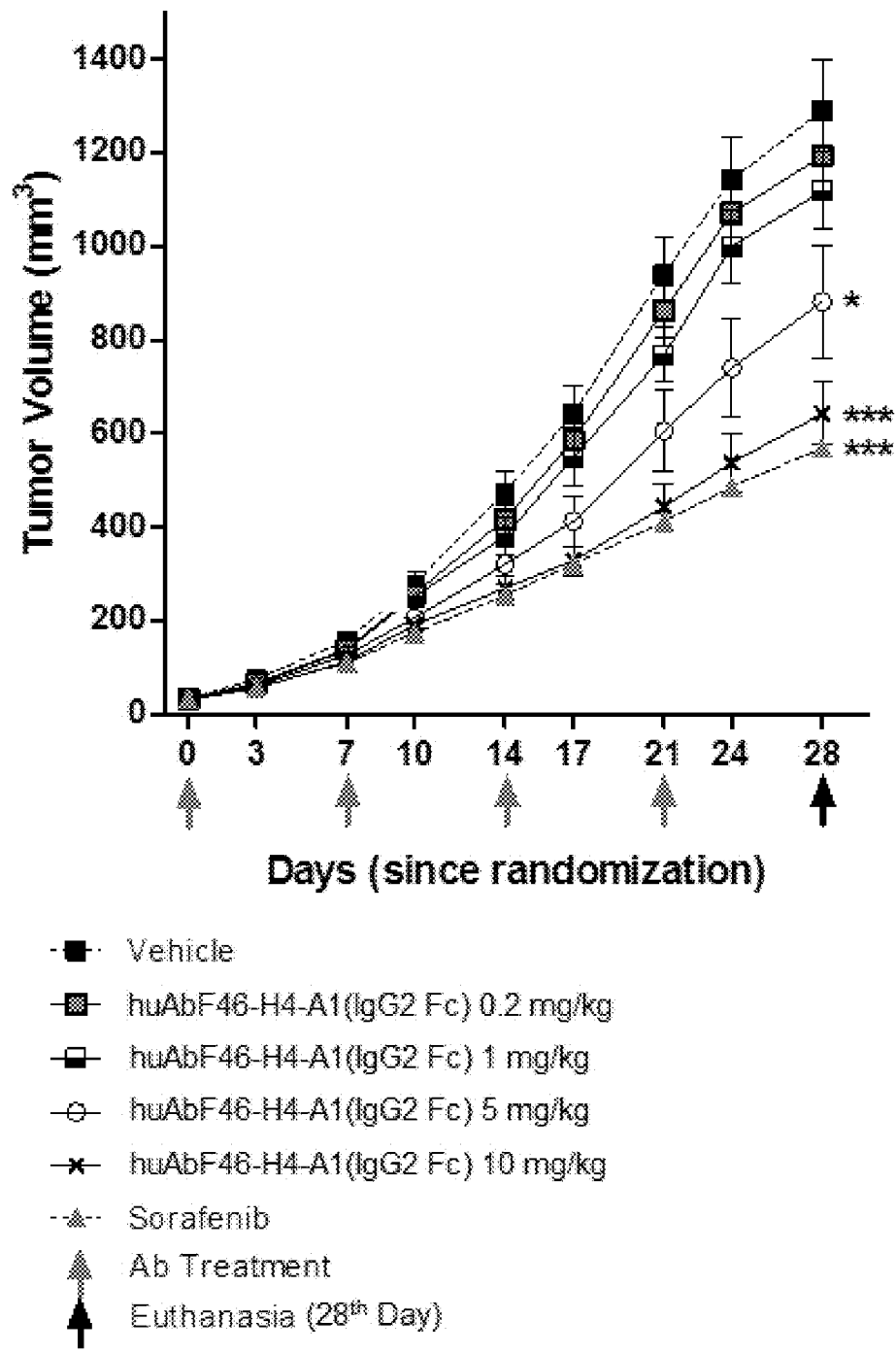
FIG. 13 is a graph of tumor volume plotted against time (days), showing in vivo anti-cancer effect of huAbF46-H4-A1 (IgG2 Fc) in MHCC97H liver cancer model.

The obtained results are shown in FIG. 13. In FIG. 13, tumor volumes were measured on indicated days are plotted (mean and s.e.m.) for treatment groups (huAbF46-H4-A1 (IgG2 Fc)) and vehicle (negative control) group. Asterisks (*) represent P-values versus vehicle group according to repeated measures ANOVA, plotted for the last day only (*P<0.05, P<0.01, *P<0.001, ****P<0.0001). As shown in FIG. 13, treatment with huAbF46-H4-A1 (IgG2 Fc) 5 mg/kg significantly inhibited tumor growth starting from the 14$^{th}$ day (p<0.05) and throughout the remainder of the study (p<0.01). Treatment with huAbF46-H4-A1 (IgG2 Fc) 10 mg/kg significantly inhibited tumor growth starting from the 3$^{rd}$ day (p<0.05) and throughout the remainder of the study (p<0.01). Treatment with huAbF46-H4-A1 (IgG2 Fc) at 5 and 10 mg/kg also significantly reduced tumor weight (p<0.01 or p<0.05, respectively) compared to the PBS vehicle group. The positive control drug sorafenib at 30 mg/kg given daily and huAbF46-H4-A1 (IgG2 Fc) at 5 and 10 mg/kg demonstrated significant inhibition of MHCC97H tumor growth, whereas other treatments resulted in no significant inhibitory effect on tumor growth. Furthermore, huAbF46-H4-A1 (IgG2 Fc) treatment showed a dose-response relationship with respect to tumor volume, relative tumor volume and tumor weight reductions compared to the control group. In conclusion, treatment with huAbF46-H4-A1 (IgG2 Fc) showed anti-tumor efficacy in this human liver cancer MHCC97H xenograft model.

Example 18: Anticancer Effect of huAbF46-H4-A1 (IgG2 Fc) on PDT Cell Line

Tumor xenograft study using patient-derived tumor (PDT; NSCLC and RCC) was performed using 5-7 weeks old male NRMI nu/nu mice. The tumor fragments passaged in vivo in donor mice were collected, made into equally-sized fragments, and implanted subcutaneously into the flank region of the recipient mice under anesthesia. When the average tumor size was 50-250 mm3, mice were randomized into either huAbF46-H4-A1 (IgG2 Fc) (5 mg/kg I.V. once a week) treatment group, or vehicle (PBS I.V. once a week) treatment group. Each group consisted of 10 mice. Tumor volumes and body weights were measured two to three times a week for total study period about 6 weeks. The tumor volume (V) was calculated as follows: V (mm3)=[long axis length (mm)×(short axis length (mm))$^2$]/2. At the end of the in vivo phase, the mice were euthanized; tumors were extracted and fixed in 10% formaldehyde or frozen for further analysis. Tumor growth inhibition was calculated as follows: 100−100*(ΔTV in huAbF46-H4-A1 (IgG2 Fc) group)/(ΔTV in Vehicle group), where ΔTV=TV(end)−TV (d0).

Figure 14:
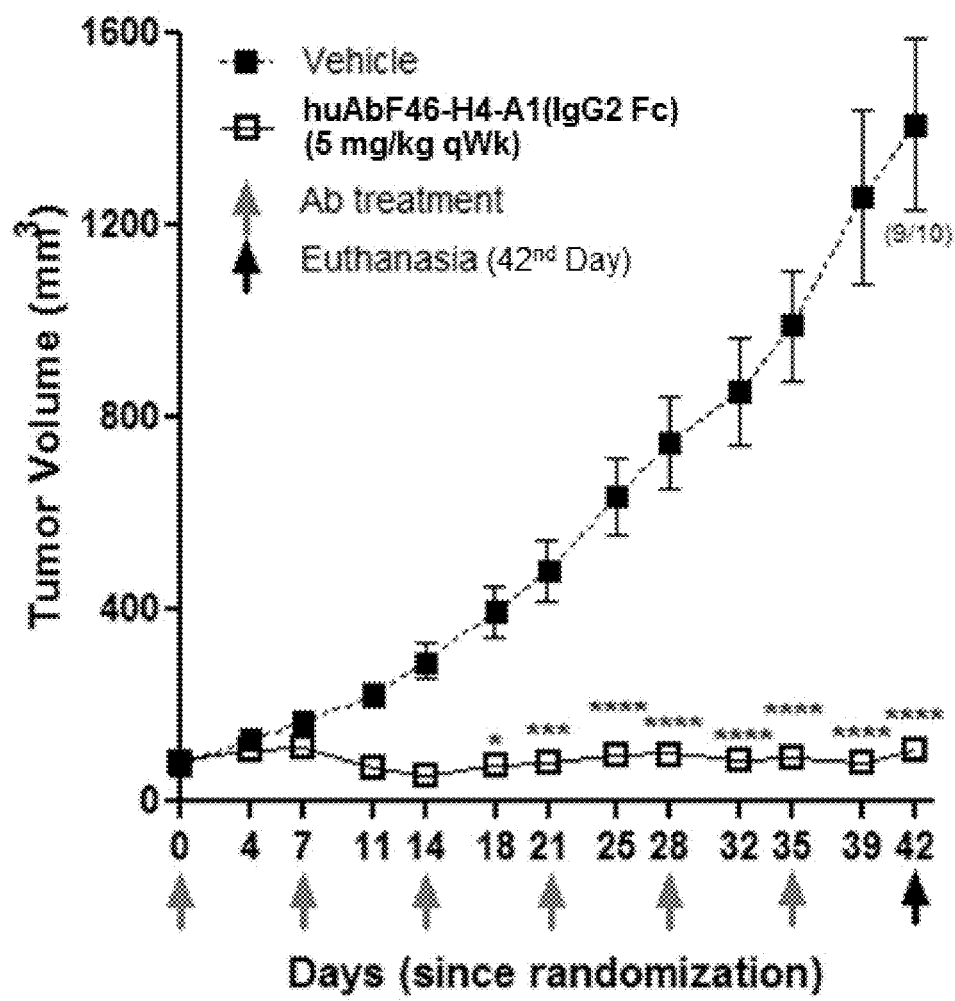
FIGS. 14 and 15 are graphs of tumor volume plotted against time (days), showing in vivo anti-cancer effect of huAbF46-H4-A1 (IgG2 Fc) in PDT (patient-derived tumor) xenograft models.
Figure 15:
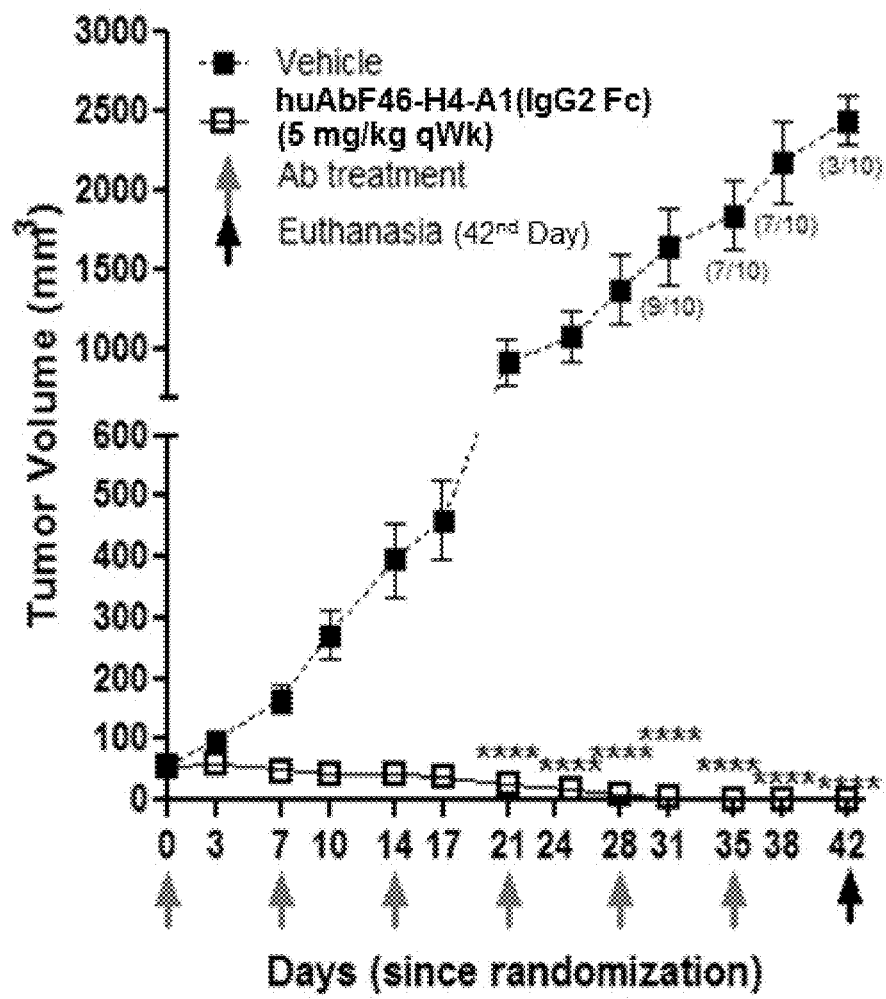
Figure 16:
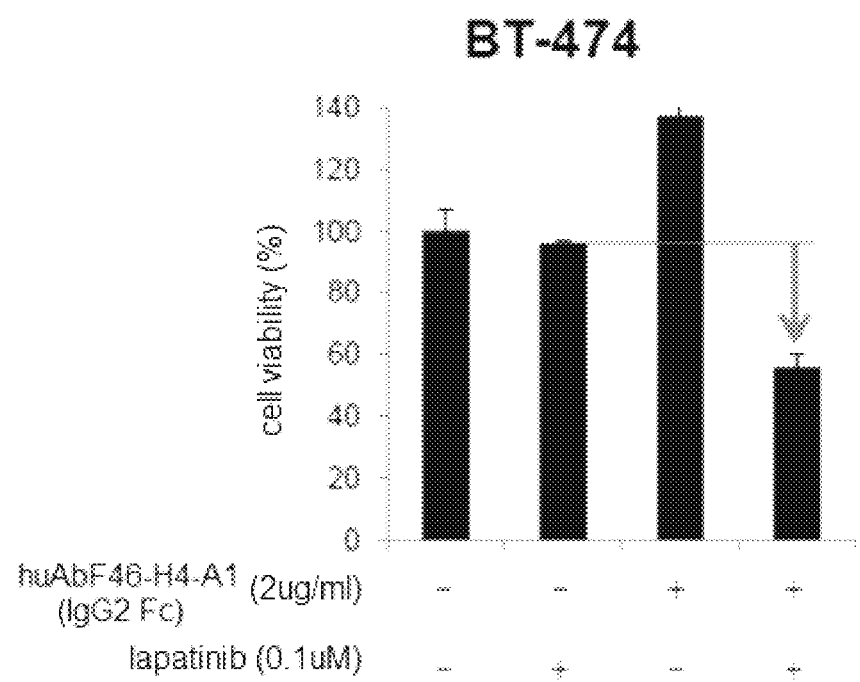
FIGS. 16-19 are graphs showing the cell viability of four breast cancer cell lines treated with huAbF46-H4-A1 and lapatinib, alone and in combination: BT-474 (FIG. 16), HCC1806 (FIG. 17), HCC1954 (FIG. 18), and colorectal cancer cell line HT29 (FIG. 19).
Figure 17:
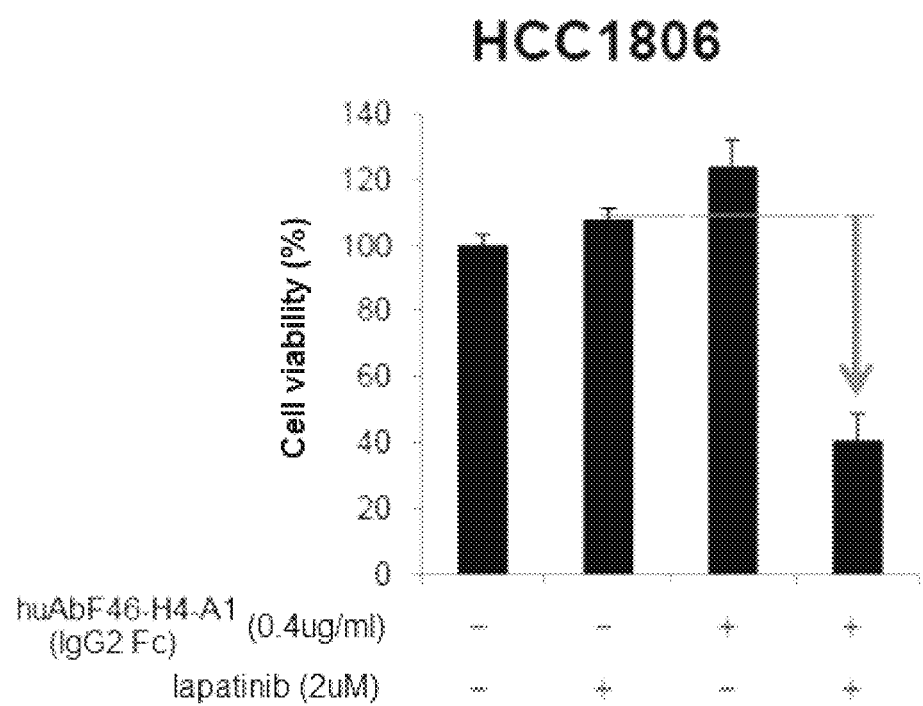
Figure 18:
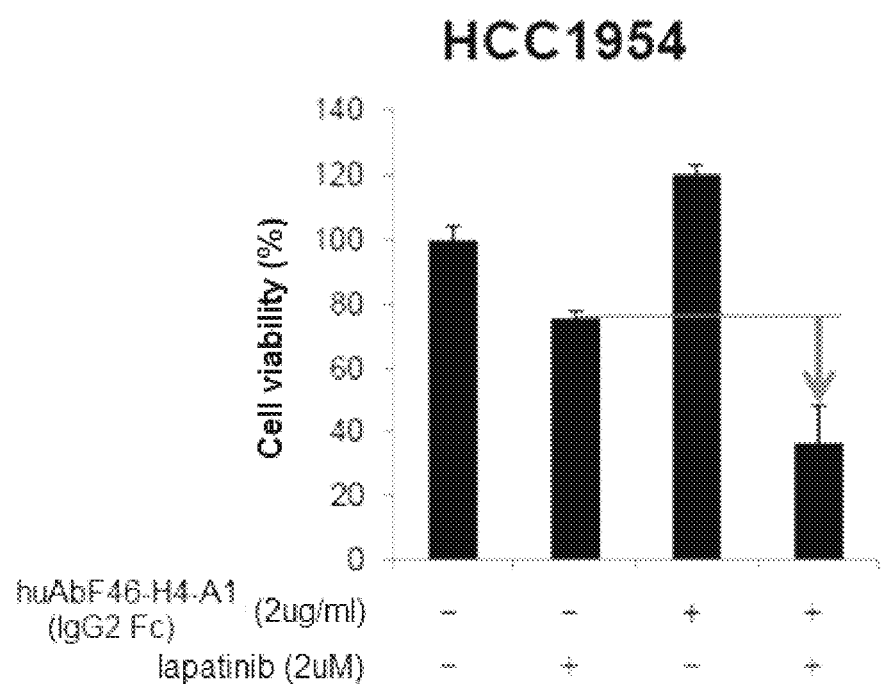
Figure 19:
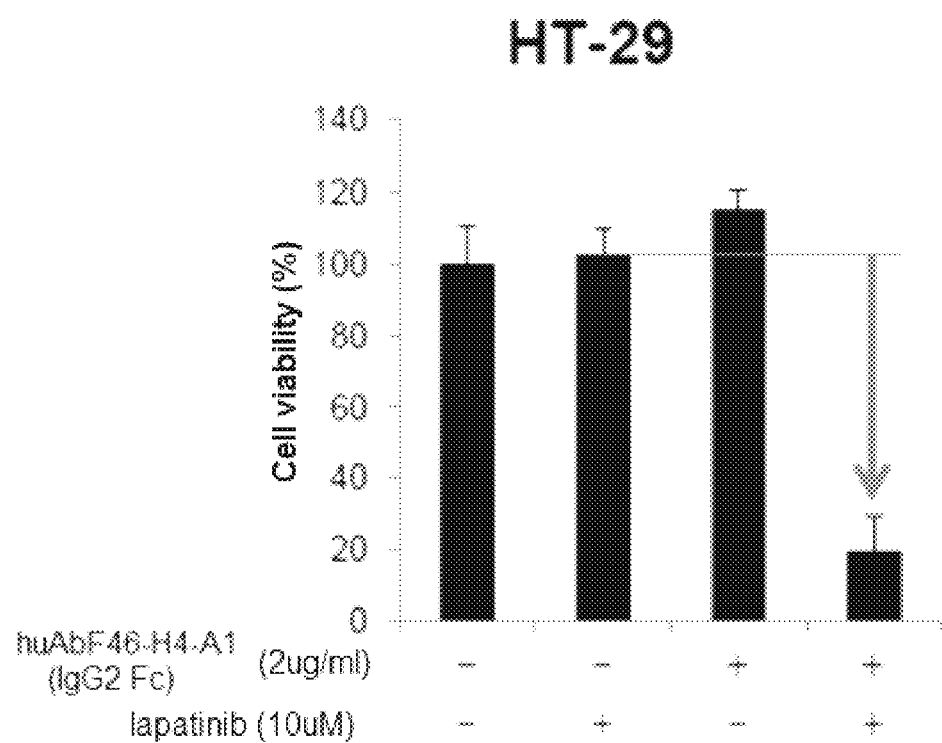

The obtained results are shown in FIGS. 14 (NSCLC) and 15 (RCC). In FIGS. 14 and 15, tumor volumes were measured on indicated days are plotted (mean and SEM) for the two groups (Vehicle or huAbF46-H4-A1 (IgG2 Fc)). Asterisks (*) represent p values versus Vehicle group according to repeated measures ANOVA (*: p<0.05, : p<0.01, *: p<0.001, **: p<0.0001). Numbers inside parenthesis shows remaining mice at each time point, as mice were euthanized before the end of the study when TV reached 2000 mm$^3$. As shown in FIGS. 14 and 15, huAbF46-H4-A1 (IgG2 Fc) showed very potent and statistically significant tumor growth inhibition in the PDT model. huAbF46-H4-A1 (IgG2 Fc) caused tumor growth arrest, and even complete regression, in these models. In these examples (one NSCLC model (FIG. 14), one RCC model (FIG. 15**)), huAbF46-H4-A1 (IgG2 Fc) treatment resulted in tumor volume inhibitions of 100% and 98%, respectively.

Example 19: Synergistic Effect by Combined Treatment Using huAbF46-H4-A1 (IgG2 Fc) with Lapatinib, Regorafenib, or Vemurafenib Cell proliferation in response to antibody treatment in vitro was assessed by a CTG (Promega) assay according to manufacturer's instructions. EBC1, HT-29, BT-474, HCC1806, HCC1954 and MKN45 cells were respectively plated at a density of 5×10$^3$ cells per well in FBS 10% (v/v) RPMI 1640 medium (Gibco) onto a 96-well plate (BD). The HT-29 (HTB-38), BT-474 (HTB-20), HCC1806 (CRL-2335) and HCC1954 (CRL-2338) cell lines were all purchased from ATCC. MKN45 (JCRB0254) and EBC1 (JCRB0820) cell lines were purchased from the Health Science Research Resource Bank. After 24 hours incubation, the c-Met targeting antibody huAbF46-H4-A1 (IgG2 Fc) was added alone or in combination with another drug (lapatinib, regorafenib or vemurafenib) diluted in 10% FBS (v/v) RPMI medium. Lapatinib, regorafenib and vemurafenib were purchased from Selleck Chemicals.

For the combination treatment of each experiment, IC$_{20}$ concentration of one drug (drug A) and differing amounts of the other drug (drug B) were treated to see if the efficacy of drug B is improved by combi-treatment with drug A in a dose-dependent manner (see FIGS. 16-22). After 72 hours incubation, 100 μL of the CTG reagent (Promega) was added to each well followed by incubation at 37° C. for 30 minutes. The luminescence was measured using an Envision Multi-label Plate Reader (Perkin Elmer).

Figure 20:
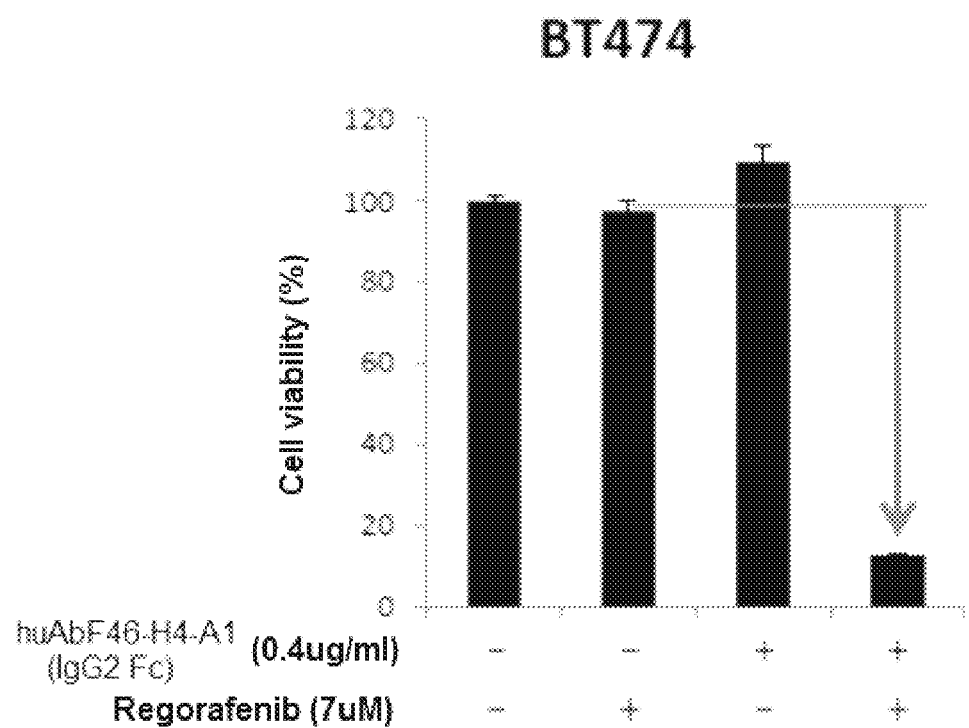
FIG. 20 is a graph showing the cell viability of a breast cancer cell line BT-474 treated with huAbF46-H4-A1 (IgG2 Fc) and regorafenib, alone and in combination with each other.
Figure 21:
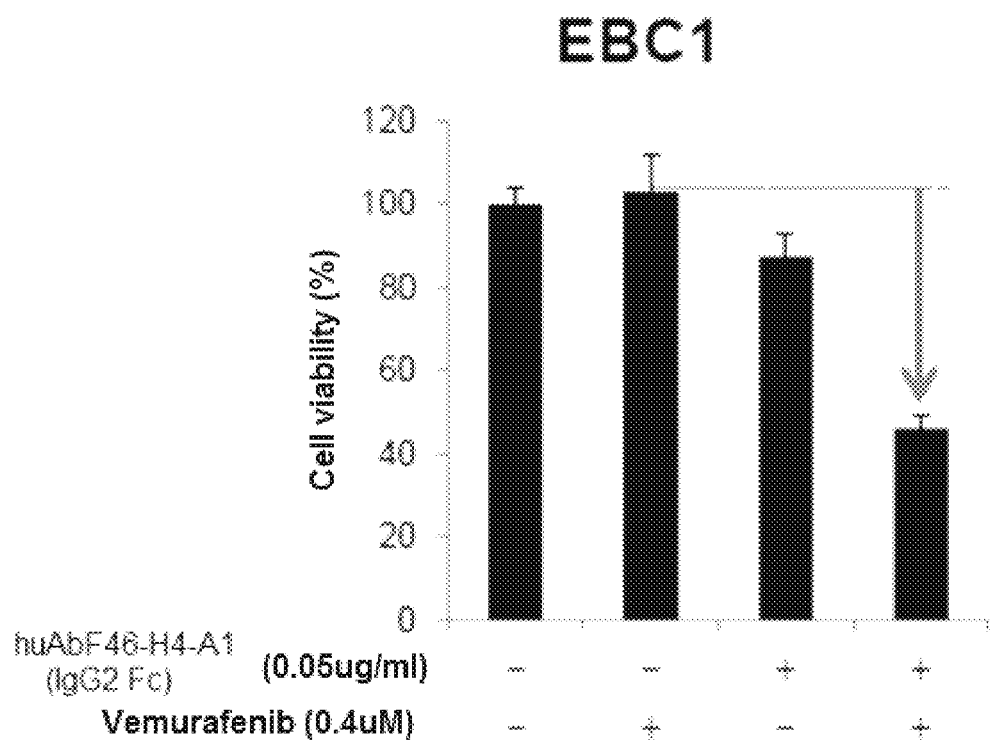
FIGS. 21 and 22 are graphs showing the cell viability of a lung cancer cell line EBC1 (FIG. 21) and a gastric cancer cell line MKN45 (FIG. 22), when treated with huAbF46-H4-A1 (IgG2 Fc) and vemurafenib, alone and in combination with each other.
Figure 22:
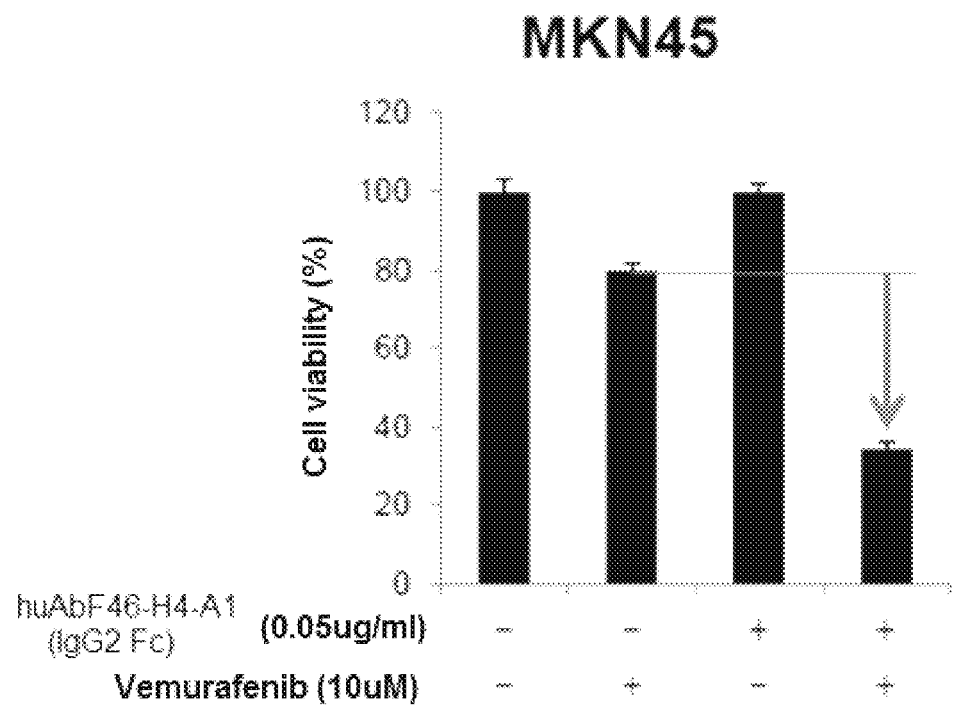

The obtain results were shown in FIGS. 16-22. FIGS. 16-19 show the cell viability of breast cancer cell lines BT-474 (FIG. 16), HCC1806 (FIG. 17), HCC1954 (FIG. 18), and colorectal cancer cell line HT29 (FIG. 19), respectively, when huAbF46-H4-A1 (IgG2 Fc) and lapatinib are treated alone or in combination with each other. As shown in FIGS. 16-19, anti-tumor efficacy of lapatinib was significantly improved when co-treated with huAbF46-H4-A1 (IgG2 Fc). FIG. 20 shows the cell viability of a breast cancer cell line BT-474 when treated with huAbF46-H4-A1 (IgG2 Fc) and regorafenib alone or in combination with each other. As shown in FIG. 20, anti-tumor efficacy of regorafenib was significantly improved when co-treated with huAbF46-H4-A1 (IgG2 Fc). FIGS. 21 and 22 show the cell viability of a lung cancer cell line EBC1 (FIG. 21) and a gastric cancer cell line MKN45 (FIG. 22) when treated with huAbF46-H4-A1 (IgG2 Fc) and vemurafenib alone or in combination with each other. As shown in FIGS. 21 and 22, anti-tumor efficacy of vemurafenib was significantly improved when co-treated with huAbF46-H4-A1 (IgG2 Fc).

As described above, according to the anti-c-Met antibody and the pharmaceutical composition for preventing or treating cancer including the same according to one or more embodiments of the present invention, cancer may be effectively prevented or treated.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treatment of a cancer, comprising co-administering (a) an anti-c-Met antibody or an antigen-binding fragment thereof, and (b) at least one of lapatinib, regorafenib, vemurafenib or a combination thereof, to a subject in need of treatment of the cancer;
   wherein the cancer is associated with c-Met activity or overexpression of c-Met; and
   wherein the anti-c-Met antibody or antigen-binding fragment thereof comprises:
   a heavy chain variable region comprising (a) a complementarity determining region-H1 (CDR-H1) having an amino acid sequence consisting of SEQ ID NO: 1, (b) a CDR-H2 having an amino acid sequence consisting of SEQ ID NO: 2, and (c) a CDR-H3 having an amino acid sequence consisting of SEQ ID NO: 3; and
   a light chain variable region comprising: (a) a CDR-L1 having an amino acid sequence consisting of SEQ ID NO: 10 or 71, (b) a CDR-L2 having an amino acid sequence consisting of SEQ ID NO: 11, and (c) a CDR-L3 having an amino acid sequence comprising SEQ ID NO: 13, 14, 15, or 16.

2. The method of claim 1, wherein the anti-c-Met antibody or an antigen-binding fragment thereof, and the at least one of lapatinib, regorafenib, vemurafenib, or combination thereof, are administered simultaneously or sequentially in any order.

3. The method of claim 1, wherein the light chain variable region comprises
   CDR-L1 having an amino acid sequence of SEQ ID NO: 10, CDR-L2 having an amino acid sequence of SEQ ID NO: 11, and CDR-L3 having an amino acid sequence of SEQ ID NO: 13, 14, 15, or 16; or CDR-L1 having an amino acid sequence of SEQ ID NO: 71, CDR-L2 having an amino acid sequence of SEQ ID NO: 11, and CDR-L3 having an amino acid sequence of SEQ ID NO: 13.

4. The method of claim 1, wherein the anti-c-Met antibody or antigen-binding fragment thereof comprises the heavy chain variable region has an amino acid sequence of SEQ ID NO: 17, and the light chain variable region has an amino acid sequence of SEQ ID NO: 74, 18, 19, 20, 21, or 72.

5. The method of claim 1, wherein the anti-c-Met antibody or antigen-binding fragment thereof comprises:

a heavy chain comprising an amino acid sequence from $18^{th}$ to $462^{nd}$ of SEQ ID NO: 62, an amino acid sequence from $18^{th}$ to $461^{st}$ of SEQ ID NO: 64, or amino acid sequence from $18^{th}$ to $460^{th}$ of SEQ ID NO: 66, and a light chain comprising an amino acid sequence from $21^{st}$ to $220^{th}$ of SEQ ID NO: 68;

a heavy chain comprising an amino acid sequence from $18^{th}$ to $462^{nd}$ of SEQ ID NO: 62, an amino acid sequence from $18^{th}$ to $461^{st}$ of SEQ ID NO: 64, or amino acid sequence from $18^{th}$ to $460^{th}$ of SEQ ID NO: 66, and a light chain comprising an amino acid sequence from $21^{st}$ to $220^{th}$ of SEQ ID NO: 70; or a heavy chain comprising an amino acid sequence from $18^{th}$ to $462^{nd}$ of SEQ ID NO: 62, an amino acid sequence from $18^{th}$ to $461^{st}$ of SEQ ID NO: 64, or amino acid sequence from $18^{th}$ to $460^{th}$ of SEQ ID NO: 66, and a light chain comprising an amino acid sequence of SEQ ID NO: 73.

6. The method for treatment of a cancer of claim 1, wherein the cancer is breast cancer, colon cancer, lung cancer, kidney cancer, or gastric cancer.

* * * * *

SEQUENCE LISTING

<160> NUMBER OF SEQ ID NOS: 74

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: UNSURE
<222> LOCATION: (1)
<223> OTHER INFORMATION: Xaa is Pro or Ser
<220> FEATURE:
<221> NAME/KEY: UNSURE
<222> LOCATION: (2)
<223> OTHER INFORMATION: Xaa is Glu or Asp

<400> SEQUENCE: 4

Xaa Xaa Tyr Tyr Met Ser
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: UNSURE
<222> LOCATION: (3)
<223> OTHER INFORMATION: X is Asn or Lys
<220> FEATURE:
<221> NAME/KEY: UNSURE
<222> LOCATION: (4)
<223> OTHER INFORMATION: Xaa is Ala or Val

```
<220> FEATURE:
<221> NAME/KEY: UNSURE
<222> LOCATION: (7)
<223> OTHER INFORMATION: Xaa is Asn or Thr

<400> SEQUENCE: 5

Ala Asn Xaa Xaa Asn Gly Xaa Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: UNSURE
<222> LOCATION: (5)
<223> OTHER INFORMATION: Xaa is Ser or Thr

<400> SEQUENCE: 6

Asp Asn Trp Leu Xaa Tyr
 1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: UNSURE
<222> LOCATION: (4)
<223> OTHER INFORMATION: Xaa is His, Arg, Gln or Lys
<220> FEATURE:
<221> NAME/KEY: UNSURE
<222> LOCATION: (9)
<223> OTHER INFORMATION: Xaa is Ser or Trp
<220> FEATURE:
<221> NAME/KEY: UNSURE
<222> LOCATION: (12)
<223> OTHER INFORMATION: Xaa is His or Gln
<220> FEATURE:
<221> NAME/KEY: UNSURE
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
 1               5                  10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: UNSURE
<222> LOCATION: (2)
<223> OTHER INFORMATION: Xaa is Ala or Gly
<220> FEATURE:
<221> NAME/KEY: UNSURE
<222> LOCATION: (4)
<223> OTHER INFORMATION: Xaa is Thr or Lys
<220> FEATURE:
<221> NAME/KEY: UNSURE
<222> LOCATION: (7)
<223> OTHER INFORMATION: Xaa is Ser or Pro

<400> SEQUENCE: 8
```

```
Trp Xaa Ser Xaa Arg Val Xaa
  1               5
```

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: UNSURE
<222> LOCATION: (1)
<223> OTHER INFORMATION: Xaa is Gly, Ala or Gln
<220> FEATURE:
<221> NAME/KEY: UNSURE
<222> LOCATION: (6)
<223> OTHER INFORMATION: Xaa is Arg, His, Ser, Ala, Gly or Lys
<220> FEATURE:
<221> NAME/KEY: UNSURE
<222> LOCATION: (8)
<223> OTHER INFORMATION: Xaa is Leu, Tyr, Phe or Met

<400> SEQUENCE: 9

```
Xaa Gln Ser Tyr Ser Xaa Pro Xaa Thr
  1               5
```

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

```
Lys Ser Ser Gln Ser Leu Leu Ala Ser Gly Asn Gln Asn Asn Tyr Leu
  1               5                  10                  15

Ala
```

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

```
Trp Ala Ser Thr Arg Val Ser
  1               5
```

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

```
Gln Gln Ser Tyr Ser Ala Pro Leu Thr
  1               5
```

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

-continued

```
Gln Gln Ser Tyr Ser Arg Pro Tyr Thr
  1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
  1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
  1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
  1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115
```

-continued

```
<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18
```

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

```
<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19
```

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

```
<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20
```

Asp Ile Gln Met Thr Gln Ser Pro Ser Ser Leu Ser Ala Ser Val Gly

```
            1               5                  10                 15
Asp Arg Val Thr Ile Thr Cys Lys Ser Ser Gln Ser Leu Leu Ala Ser
                        20                  25                  30

Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
                100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
                100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23
```

Pro Asp Tyr Tyr Met Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

```
Lys Ser Ser Arg Ser Leu Leu Ser Ser Gly Asn His Lys Asn Tyr Leu
  1               5                  10                  15

Ala
```

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

```
Lys Ser Ser Lys Ser Leu Leu Ala Ser Gly Asn Gln Asn Asn Tyr Leu
  1               5                  10                  15

Ala
```

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

```
Lys Ser Ser Arg Ser Leu Leu Ala Ser Gly Asn Gln Asn Asn Tyr Leu
  1               5                  10                  15

Ala
```

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

```
Lys Ser Ser His Ser Leu Leu Ala Ser Gly Asn Gln Asn Asn Tyr Leu
  1               5                  10                  15

Ala
```

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

```
Trp Ala Ser Lys Arg Val Ser
  1               5
```

<210> SEQ ID NO 35

```
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
 1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
 1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttttctcg taacactttt aaatggtatc      60
cagtgtgagg tgaagctggt ggagtctgga ggaggcttgg tacagcctgg gggttctctg     120
```

```
agactctcct gtgcaacttc tgggttcacc ttcactgatt actacatgag ctgggtccgc      180
cagcctccag gaaaggcact tgagtggttg ggttttatta gaaacaaagc taatggttac      240
acaacagagt acagtgcatc tgtgaagggt cggttcacca tctccagaga taattcccaa      300
agcatcctct atcttcaaat ggacaccctg agagctgagg acagtgccac ttattactgt      360
gcaagagata actggtttgc ttactggggc caagggactc tggtcactgt ctctgcagct      420
agcaccaagg gcccatcggt cttccccctg gcaccctcct ccaagagcac ctctgggggc      480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac ccagacctac      660
atctgcaacg tgaatcacaa gcccagcaac accaaggtgg acaagaaagt tgagcccaaa      720
tcttgtgaca aaactcacac atgcccaccg tgcccagcac ctgaactcct ggggggaccg      780
tcagtcttcc tcttcccccc aaaacccaag gacaccctca tgatctcccg gacccctgag      840
gtcacatgcg tggtggtgga cgtgagccac gaagaccctg aggtcaagtt caactggtac      900
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080
gccaaagggc agccccgaga accacaggtg tacaccctgc ccccatcccg ggaggagatg     1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga ctcgag                               1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of
      chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference

```
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga gaaggtcact atgagctgca agtccagtca gagtctttta     180
gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                           759

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
                390                 395                 400
385

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125
```

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

```
Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
```

```
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
 1               5                  10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110
```

```
Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 219
<212> TYPE: PRT
<213> ORGANISM: Artificial Sequence
```

<220> FEATURE:
<223> OTHER INFORMATION: Synthetic amino acid sequence of H4-light

<400> SEQUENCE: 46

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215
```

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
```

| | |
|---|---|
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

| | |
|---|---|
| gaggtgcagc tggtggagtc tgggggaggc ttggtccagc ctggagggtc cctgagactc | 60 |
| tcctgtgcag cctctggatt caccttcact gactactaca tgagctgggt ccgccaggct | 120 |
| ccagggaagg ggctggagtg gttgggcttt attagaaaca agctaacgg ttacaccaca | 180 |
| gaatacagtg cgtctgtgaa aggcagattc accatctcaa gagataattc aaagaactca | 240 |
| ctgtatctgc aaatgaacag cctgcgtgct gaggacacgg ccgtgtatta ctgtgctaga | 300 |
| gataactggt tgcttactg gggtcaagga accctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc caggggctc actccgtttg      60
tcctgtgcag cttctggctt caccttcact gattactaca tgagctgggt gcgtcaggcc     120
ccgggtaagg gcctggaatg gttgggtttt attagaaaca agctaatgg ttacacaaca      180
gagtacagtg catctgtgaa gggtcgtttc actataagca gagataattc caaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg ggcacagcg      420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcggagg agcagtacaa cagcacgtac      900
cgtgtggtca gcgtcctcac cgtcctgcac caggactggc tgaatggcaa ggagtacaag     960
tgcaaggtct ccaacaaagc cctcccagcc ccatcgaga aaaccatctc caaagccaaa     1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctccctgt ctccgggtaa atgactcgag                                      1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

```
gacatcgtga tgacccagtc tccagactcc ctggctgtgt ctctgggcga gagggccacc      60
atcaactgca gtccagcca gagtcttta gctagcggca accaaaataa ctacttagct      120
tggcaccagc agaaaccagg acagcctcct aagatgctca ttatttgggc atctacccgg     180
gtatccgggg tccctgaccg attcagtggc agcgggtctg gacagattt cactctcacc     240
atcagcagcc tgcaggctga agatgtgca gtttattact gtcagcaatc ctatagtgct     300
cctctcacgt tcggaggcgg taccaaggtg gagatcaaac gtacggtggc tgcaccatct     360
```

| | |
|---|---|
| gtcttcatct tcccgccatc tgatgagcag ttgaaatctg aactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga acacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51

| | |
|---|---|
| gatattgtga tgacccagac tccactctcc ctgcccgtca cccctggaga gccggcctcc | 60 |
| atctcctgca gtccagtca gagtctttta gctagtggga ccaaaataa ctacttggcc | 120 |
| tggcacctgc agaagccagg gcagtctcca cagatgctga tcatttgggc atccactagg | 180 |
| gtatctggag tcccagacag gttcagtggc agtgggtcag gcactgattt cacactgaaa | 240 |
| atcagcaggg tggaggctga ggatgttgga gtttattact gccagcagtc ctacagcgct | 300 |
| ccgctcacgt tcggacaggg taccaagctg gagctcaaac gtacggtggc tgcaccatct | 360 |
| gtcttcatct cccgccatc tgatgagcag ttgaaatctg aactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga acacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

| | |
|---|---|
| gacatcgtga tgacccagtc tccagactcc ctggctgtgt ctctgggcga gagggccacc | 60 |
| atcaactgca gtccagcca gagtctttta gctagcggca ccaaaataa ctacttagct | 120 |
| tggtaccagc agaaaccagg acagcctcct aagctgctca tttatttggc atctacccgg | 180 |
| gtatccgggg tccctgaccg attcagtggc agcgggtctg gacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct cccgccatc tgatgagcag ttgaaatctg aactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga acacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

```
gatatccaga tgacccagtc cccgagctcc ctgtccgcct ctgtgggcga tagggtcacc    60
atcacctgca agtccagtca gagtctttta gctagtggca accaaaataa ctacttggcc   120
tggcaccaac agaaaccagg aaaagctccg aaaatgctga ttatttgggc atccactagg   180
gtatctggag tccttctcg cttctctgga tccgggtctg gacggattt cactctgacc     240
atcagcagtc tgcagccgga agacttcgca acttattact gtcagcagtc ctacagcgct   300
ccgctcacgt tcggacaggg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc   600
gaagtcaccc atcagggcct gagctcgccc gtcacaaaga gcttcaacag gggagagtgt   660
tgactcgag                                                           669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

```
gctagcgttt tagcagaagt tcaattggtt gaatctggtg gtggtttggt tcaaccaggt    60
ggttctttga gattgtcttg tgctgcttct ggttttactt tcaccgatta ttacatgtcc   120
tgggttagac aagctccagg taaggtttg gaatggttgg gtttcattag aaacaaggct   180
aacggttaca ctaccgaata ttctgcttct gttaagggta gattcaccat ttctagagac   240
aactctaaga cacccttgta cttgcaaatg aactccttga gagctgaaga tactgctgtt   300
tattactgcg ctagagataa ttggttgct tattgggtc aaggtacttt ggttactgtt   360
tcttctggcc tcgggggcct cggaggagga ggtagtggcg aggaggctc cggtggatcc   420
agcggtgtgg gttccgatat tcaaatgacc caatctccat cttctttgtc tgcttcagtt   480
ggtgatagag ttaccattac ttgtaagtcc tcccaatctt tgttggcttc tggtaatcag   540
```

-continued

```
aacaattact tggcttggca tcaacaaaaa ccaggtaaag ctccaaagat gttgattatt    600
tgggcttcta ccagagtttc tggtgttcca tctagatttt ctggttctgg ttccggtact    660
gattttactt tgaccatttc atccttgcaa ccagaagatt tcgctactta ctactgtcaa    720
caatcttact ctgctccatt gacttttggt caaggtacaa aggtcgaaat caagagagaa    780
ttcggtaagc ctatccctaa ccctctcctc ggtctcgatt ctacgggtgg tggtggatct    840
ggtggtggtg ttctggtgg tggtggttct caggaactga caactatatg cgagcaaatc    900
ccctcaccaa ctttagaatc gacgccgtac tctttgtcaa cgactactat tttggccaac    960
gggaaggcaa tgcaaggagt ttttgaatat tacaaatcag taacgtttgt cagtaattgc   1020
ggttctcacc cctcaacaac tagcaaaggc agccccataa acacacagta tgtttttga   1080 gtttaaac                                                            1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
```

```
ttagttttttt agccttattt ctggggtaat taatcagcga agcgatgatt tttgatctat        300
taacagatat ataaatgcaa aaactgcata accactttaa ctaatacttt caacattttc         360
ggtttgtatt acttcttatt caaatgtaat aaaagtatca acaaaaaatt gttaatatac         420
ctctatactt taacgtcaag gagaaaaaac cccggatcgg actactagca gctgtaatac         480
gactcactat agggaatatt aagctaattc tacttcatac attttcaatt aagatgcagt         540
tacttcgctg ttttcaata ttttctgtta ttgctagcgt tttagcagaa gttcaattgg          600
ttgaatctgg tggtggtttg gttcaaccag gtggttcttt gagattgtct tgtgctgctt        660
ctggttttac tttcaccgat tattacatgt cctgggttag acaagctcca ggtaaaggtt         720
tggaatggtt gggtttcatt agaaacaagg ctaacggtta cactaccgaa tattctgctt        780
ctgttaaggg tagattcacc atttctagag acaactctaa gaacaccttg tacttgcaaa        840
tgaactcctt gagagctgaa gatactgctg tttattactg cgctagagat aattggtttg        900
cttattgggg tcaaggtact ttggttactg tttcttctgg cctcgggggc tcggaggag         960 gaggtagtgg cggaggaggc tccggtggat ccagcggtgt gggttccgat attcaaatga       1020
cccaatctcc atcttctttg tctgcttcag ttggtgatag agttaccatt acttgtaagt       1080
cctcccaatc tttgttggct tctggtaatc agaacaatta cttggcttgg catcaacaaa       1140
aaccaggtaa agctccaaag atgttgatta tttgggcttc taccagagtt tctggtgttc       1200
catctagatt ttctggttct ggttccggta ctgattttac tttgaccatt tcatccttgc       1260
aaccagaaga tttcgctact tactactgtc aacaatctta ctctgctcca ttgacttttg       1320
gtcaaggtac aaaggtcgaa atcaagagag aattcggtaa gcctatccct aaccctctcc      1380
tcggtctcga ttctacgggt ggtggtggat ctggtggtgg tggttctggt ggtggtggtt      1440
ctcaggaact gacaactata tgcgagcaaa tcccctcacc aactttagaa tcgacgccgt       1500
actctttgtc aacgactact attttggcca acgggaaggc aatgcaagga gttttttgaat      1560 attacaaatc agtaacgttt gtcagtaatt gcggttctca cccctcaaca actagcaaag      1620
gcagccccat aaacacacag tatgtttttt gagtttaaac ccgctgatct gataacaaca       1680
gtgtagatgt aacaaaatcg actttgttcc cactgtactt ttagctcgta caaaatacaa       1740
tatacttttc atttctccgt aaacaacatg ttttcccatg taatatcctt ttctatttt        1800 cgttccgtta ccaactttac acatacttta tatagctatt cacttctata cactaaaaaa      1860
ctaagacaat tttaattttg ctgcctgcca tatttcaatt tgttataaat tcctataatt       1920
tatcctatta gtagctaaaa aaagatgaat gtgaatcgaa tcctaagaga attgggcaag      1980
tgcacaaaca atacttaaat aaatactact cagtaataac ctatttctta gcatttttga      2040
cgaaatttgc tattttgtta gagtcttta caccatttgt ctccacacct ccgcttacat       2100
caacaccaat aacgccattt aatctaagcg catcaccaac attttctggc gtcagtccac      2160
cagctaacat aaaatgtaag ctctcggggc tctcttgcct tccaacccag tcagaaatcg      2220
agttccaatc caaaagttca cctgtcccac ctgcttctga atcaaacaag ggaataaacg      2280
aatgaggttt ctgtgaagct gcactgagta gtatgttgca gtcttttgga aatacgagtc      2340
ttttaataac tggcaaaccg aggaactctt ggtattcttg ccacgactca tctccgtgca      2400
gttggacgat atcaatgccg taatcattga ccagagccaa acatcctcc ttaggttgat       2460 tacgaaacac gccaaccaag tatttcggag tgcctgaact attttttatat gcttttacaa      2520 gacttgaaat tttccttgca ataaccgggt caattgttct ctttctattg ggcacacata      2580
```

```
taatacccag caagtcagca tcggaatcta gagcacattc tgcggcctct gtgctctgca      2640
agccgcaaac tttcaccaat ggaccagaac tacctgtgaa attaataaca gacatactcc      2700
aagctgcctt tgtgtgctta atcacgtata ctcacgtgct caatagtcac caatgccctc      2760
cctcttggcc ctctccttt cttttttcga ccgaatttct tgaagacgaa agggcctcgt       2820
gatacgccta tttttatagg ttaatgtcat gataataatg gtttcttagg acggatcgct      2880
tgcctgtaac ttacacgcgc ctcgtatctt ttaatgatgg aataatttgg gaatttactc      2940
tgtgtttatt tattttatg ttttgtattt ggattttaga aagtaaataa agaaggtaga       3000
agagttacgg aatgaagaaa aaaaaataaa caaaggttta aaaaatttca acaaaaagcg      3060
tactttacat atatatttat tagacaagaa aagcagatta aatagatata cattcgatta      3120
acgataagta aaatgtaaaa tcacaggatt ttcgtgtgtg gtcttctaca cagacaagat      3180
gaaacaattc ggcattaata cctgagagca ggaagagcaa gataaaggt agtatttgtt       3240 ggcgatcccc ctagagtctt ttacatcttc ggaaaacaaa aactattttt tctttaattt      3300
ctttttttac tttctatttt taatttatat atttatatta aaaaatttaa attataatta     3360
tttttatagc acgtgatgaa aaggaccag gtggcacttt tcggggaaat gtgcgcggaa       3420
cccctatttg tttattttc taaatacatt caaatatgta tccgctcatg agacaataac       3480
cctgataaat gcttcaataa tattgaaaaa ggaagagtat gagtattcaa catttccgtg      3540
tcgcccttat tccctttttt gcggcatttt gccttcctgt ttttgctcac ccagaaacgc      3600
tggtgaaagt aaaagatgct gaagatcagt tgggtgcacg agtgggttac atcgaactgg      3660
atctcaacag cggtaagatc cttgagagtt ttcgccccga agaacgtttt ccaatgatga      3720
gcacttttaa agttctgcta tgtggcgcgg tattatcccg tgttgacgcc gggcaagagc      3780
aactcggtcg ccgcatacac tattctcaga atgacttggt tgagtactca ccagtcacag      3840
aaaagcatct tacggatggc atgacagtaa gagaattatg cagtgctgcc ataaccatga      3900
gtgataacac tgcggccaac ttacttctga caacgatcgg aggaccgaag gagctaaccg      3960
cttttttgca caacatgggg gatcatgtaa ctcgccttga tcgttgggaa ccggagctga      4020
atgaagccat accaaacgac gagcgtgaca ccacgatgcc tgtagcaatg gcaacaacgt      4080
tgcgcaaact attaactggc gaactactta ctctagcttc ccggcaacaa ttaatagact      4140
ggatggaggc ggataaagtt gcaggaccac ttctgcgctc ggcccttccg gctggctggt      4200
ttattgctga taaatctgga gccggtgagc gtgggtctcg cggtatcatt gcagcactgg      4260
ggccagatgg taagccctcc cgtatcgtag ttatctacac gacgggcagt caggcaacta      4320
tggatgaacg aaatagacag atcgctgaga taggtgcctc actgattaag cattggtaac      4380
tgtcagacca agtttactca tatatacttt agattgattt aaaacttcat ttttaattta      4440
aaaggatcta ggtgaagatc ctttttgata atctcatgac caaaatccct taacgtgagt      4500
tttcgttcca ctgagcgtca gaccccgtag aaaagatcaa aggatcttct tgagatcctt      4560 ttttttctgcg cgtaatctgc tgcttgcaaa caaaaaaacc accgctacca gcggtggttt      4620
gtttgccgga tcaagagcta ccaactcttt ttccgaaggt aactggcttc agcagagcgc      4680
agataccaaa tactgtcctt ctagtgtagc cgtagttagg ccaccacttc aagaactctg      4740
tagcaccgcc tacatacctc gctctgctaa tcctgttacc agtggctgct gccagtggcg      4800
ataagtcgtg tcttaccggg ttggactcaa gacgatagtt accggataag gcgcagcggt      4860
cgggctgaac ggggggttcg tgcacacagc ccagcttgga gcgaacgacc tacaccgaac      4920
tgagatacct acagcgtgag cattgagaaa gcgccacgct tcccgaaggg agaaaggcgg      4980
```

```
acaggtatcc ggtaagcggc agggtcggaa caggagagcg cacgaggag cttccagggg    5040 ggaacgcctg gtatctttat agtcctgtcg ggtttcgcca cctctgactt gagcgtcgat    5100
ttttgtgatg ctcgtcaggg gggccgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                   5597

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggatttc actctgacc atcagcagtc tgcagccgga agacttcgca    360
acttattact gtcagcagtc ctacagccgc ccgtacacgt tcggacaggg taccaaggtg    420
gagatcaaac gtacg                                                     435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180
```

```
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgggcagtc ctacagccgt ccgctcacgt tcggacaggg taccaaggtg    420
gagatcaaac gtacg                                                    435

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                    435

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                    435

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, U6-HC7 hinge and constant region of human IgG1
<220> FEATURE:
<221> NAME/KEY: SIGNAL
<222> LOCATION: (1)..(17)
<223> OTHER INFORMATION: signal peptide

<400> SEQUENCE: 62
```

-continued

```
Met Glu Trp Ser Trp Val Phe Leu Val Thr Leu Leu Asn Gly Ile Gln
 1               5                  10                  15

Cys Glu Val Gln Leu Val Glu Ser Gly Gly Leu Val Gln Pro Gly
             20                  25                  30

Gly Ser Leu Arg Leu Ser Cys Ala Ala Ser Gly Phe Thr Phe Thr Asp
             35                  40                  45

Tyr Tyr Met Ser Trp Val Arg Gln Ala Pro Gly Lys Gly Leu Glu Trp
         50                  55                  60

Leu Gly Phe Ile Arg Asn Lys Ala Asn Gly Tyr Thr Thr Glu Tyr Ser
 65              70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
            130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
            210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415
```

Gly Ser Phe Phe Leu Tyr Ser Lys Leu Thr Val Asp Lys Ser Arg Trp
              420                 425                 430

Gln Gln Gly Asn Val Phe Ser Cys Ser Val Met His Glu Ala Leu His
          435                 440                 445

Asn His Tyr Thr Gln Lys Ser Leu Ser Leu Ser Pro Gly Lys
      450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63

```
gaattcgccg ccaccatgga atggagctgg gttttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta agcagaga taattccaaa    300 aacacactgt acctgcagat gaacagcctg cgtgctgagg acactgccgt ctattattgt   360
gctagagata actggtttgc ttactggggc aagggactc tggtcaccgt ctcctcggct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
agctgcgatt gccactgtcc tccatgtcca gcacctgaac tcctgggggg accgtcagtc   780
ttcctcttcc ccccaaaacc caaggacacc ctcatgatct cccggacccc tgaggtcaca   840
tgcgtggtgg tggacgtgag ccacgaagac cctgaggtca agttcaactg gtacgtggac   900
ggcgtggagg tgcataatgc caagacaaag ccgcgggagg agcagtacaa cagcacgtac   960
cgtgtggtca gcgtcctcac cgtcctgcac caggactggc tgaatggcaa ggagtacaag  1020
tgcaaggtct ccaacaaagc cctcccagcc cccatcgaga aaaccatctc caaagccaaa  1080
gggcagcccc gagaaccaca ggtgtacacc ctgcccccat cccgggagga gatgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta cagcaagctc accgtggaca agagcaggtg gcagcagggg  1320
aacgtcttct catgctccgt gatgcatgag gctctgcaca accactacac gcagaagagc  1380
ctctccctgt ctccgggtaa atgactcgag                                   1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of human
      IgG1
<220> FEATURE:

```
<221> NAME/KEY: SIGNAL
<222> LOCATION: (1)..(17)
<223> OTHER INFORMATION: signal peptide

<400> SEQUENCE: 64
```

| | | | | | | | | | | | | | | |
|---|---|---|---|---|---|---|---|---|---|---|---|---|---|---|
| Met | Glu | Trp | Ser | Trp | Val | Phe | Leu | Val | Thr | Leu | Leu | Asn | Gly | Ile | Gln |
| 1 | | | | 5 | | | | | 10 | | | | | 15 | |

Cys Glu Val Gln Leu Val Glu Ser Gly Gly Gly Leu Val Gln Pro Gly
                20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Asp Val Ser His Glu Asp Pro Glu Val Lys
        275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln

```
                385                 390                395                 400
Pro Glu Asn Asn Tyr Lys Thr Thr Pro Pro Val Leu Asp Ser Asp Gly
                    405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
                435                 440                 445

His Tyr Thr Gln Lys Ser Leu Ser Leu Ser Pro Gly Lys
                450                 455                 460
```

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1

<400> SEQUENCE: 65

```
gaattcgccg ccaccatgga atggagctgg gtttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg gttttattta aaacaaagc taatggttac   240
acaacagagt acagtgcatc tgtgaagggt cgtttcacta taagcagaga taattccaaa   300
aacacactgt acctgcagat gaacagcctg cgtgctgagg acactgccgt ctattattgt   360
gctagagata actggtttgc ttactggggc caagggactc tggtcaccgt ctcctcggct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagaggaag   720
tgctgtgtgg agtgcccccc ctgcccagca cctgaactcc tggggggacc gtcagtcttc   780
ctcttccccc caaaacccaa ggacaccctc atgatctccc ggaccctga ggtcacatgc   840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc  1020
aaggtctcca acaaagccct cccagccccc atcgagaaaa ccatctccaa agccaaaggg  1080
cagccccgag aaccacaggt gtacaccctg cccccatccc gggaggagat gaccaagaac  1140
caggtcagcc tgacctgcct ggtcaaaggc ttctatccca gcgacatcgc cgtggagtgg  1200
gagagcaatg ggcagccgga gaacaactac aagaccacgc tcccgtgct ggactccgac  1260
ggctccttct tcctctacag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaatg actcgag                                      1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
     of huAbF46-H4-A1, human IgG2 hinge and constant region of human
     IgG2
<220> FEATURE:
<221> NAME/KEY: SIGNAL
<222> LOCATION: (1)..(17)
<223> OTHER INFORMATION: signal peptide

<400> SEQUENCE: 66

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365
```

Glu Met Thr Lys Asn Gln Val Ser Leu Thr Cys Leu Val Lys Gly
     370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67
gaattcgccg ccaccatgga atggagctgg gttttttctcg taacactttt aaatggtatc    60
cagtgtgagg ttcagctggt ggagtctggc ggtggcctgg tgcagccagg gggctcactc   120
cgtttgtcct gtcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta agcagagaa taattccaaa   300 aacacactgt acctgcagat gaacagcctg cgtgctgagg acactgccgt ctattattgt   360
gctagagata ctggtttgc ttactgggc aagggactc tggtcaccgt ctcctcggct   420
agcaccaagg gcccatcggt cttccccctg gcgccctgct ccaggagcac ctccgagagc   480
acagcggccc tgggctgcct ggtcaaggac tacttcccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caagggcag  1080 ccccgagaac cacaggtgta caccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacgcctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaatgact cgag                                          1404

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain of huAbF46-H4-A1(H36Y) and human kappa constant region
<220> FEATURE:
<221> NAME/KEY: SIGNAL
<222> LOCATION: (1)..(20)
<223> OTHER INFORMATION: signal peptide

<400> SEQUENCE: 68

Met Asp Ser Gln Ala Gln Val Leu Met Leu Leu Leu Ser Val Ser
 1               5                  10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide consisting of light chain of huAbF46-H4-A1(H36Y) and human kappa constant region

<400> SEQUENCE: 69
aattcactag tgattaattc gccgccacca tggattcaca ggcccaggtc ctcatgttgc    60
tgctgctatc ggtatctggt acctgtggag atatccagat gacccagtcc ccgagctccc   120
tgtccgcctc tgtgggcgat agggtcacca tcacctgcaa gtccagtcag agtcttttag   180
ctagtggcaa ccaaaataac tacttggcct ggtaccaaca gaaaccagga aaagctccga   240

```
aaatgctgat tatttgggca tccactaggg tatctggagt cccttctcgc ttctctggat    300
ccgggtctgg gacggatttc actctgacca tcagcagtct gcagccggaa gacttcgcaa    360
cttattactg tcagcagtcc tacagccgcc cgtacacgtt cggacagggt accaaggtgg    420
agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggat aacgcccctc aatcgggtaa ctcccaggag agtgtcacag    600
agcaggacag caaggacagc acctacagcc tcagcagcac cctgacgctg agcaaagcag    660
actacgagaa acacaaagtc tacgcctgcg aagtcaccca tcagggcctg agctcgcccg    720
tcacaaagag cttcaacagg ggagagtgtt gactcgag                            758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
    of huAbF46-H4-A1 and human kappa constant region
<220> FEATURE:
<221> NAME/KEY: SIGNAL
<222> LOCATION: (1)..(20)
<223> OTHER INFORMATION: signal peptide

<400> SEQUENCE: 70

```
Met Asp Ser Gln Ala Gln Val Leu Met Leu Leu Leu Leu Ser Val Ser
 1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp His Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 71
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 71

Lys Ser Ser Gln Ser Leu Leu Ala Trp Gly Asn Gln Asn Asn Tyr Leu
1               5                   10                  15

Ala

<210> SEQ ID NO 72
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 73
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile

```
                    100                 105                 110
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 74
<211> LENGTH: 114
<212> TYPE: PRT
<213> ORGANISM: Artificial Sequence
<220> FEATURE:
<223> OTHER INFORMATION: Synthetic light chain variable region of anti
      c-Met antibody

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```